(12) United States Patent
Maillere et al.

(10) Patent No.: US 7,488,791 B2
(45) Date of Patent: Feb. 10, 2009

(54) MIXTURE OF PEPTIDES DERIVED FROM E6 AND/OR E7 PAPILLOMAVIRUS PROTEINS AND USES THEREOF

(75) Inventors: Bernard Maillere, Versailles (FR); Isabelle Bourgault-Villada, Paris (FR); Sandra Pouvelle-Moratille, Sainte Geneviève des Bois (FR); Jean-Gérard Guillet, Paris (FR)

(73) Assignees: Commissariat a l'Energie Atomique, Paris (FR); Institut National de la Sante et de la Recherche Medicale (INSERM), Paris (FR)

( * ) Notice: Subject to any disclaimer, the term of this patent is extended or adjusted under 35 U.S.C. 154(b) by 350 days.

(21) Appl. No.: 10/476,570

(22) PCT Filed: May 3, 2002

(86) PCT No.: PCT/FR02/01533

§ 371 (c)(1),
(2), (4) Date: Apr. 26, 2004

(87) PCT Pub. No.: WO02/090382

PCT Pub. Date: Nov. 14, 2002

(65) Prior Publication Data

US 2004/0170644 A1    Sep. 2, 2004

(30) Foreign Application Priority Data

May 4, 2001    (FR) .................................. 01 05980

(51) Int. Cl.
*A61K 38/00* (2006.01)
(52) U.S. Cl. ..................... 530/300; 530/350; 536/23.72
(58) Field of Classification Search .............. 424/204.1; 530/300, 350; 536/23.72
See application file for complete search history.

(56) References Cited

U.S. PATENT DOCUMENTS

2005/0100928 A1*   5/2005   Hedley et al. .................. 435/6

FOREIGN PATENT DOCUMENTS

| EP | 000523391 A1 * | 6/1992 |
|---|---|---|
| WO | 00/75336 A2 | 12/2000 |

OTHER PUBLICATIONS

Isabelle Bourgault-Villada, et al. "Identification In Humans Of HPV-16 E6 and E7 Protein Epitopes Recognized By Cytolytic T Lymphocytes In Association With HLA-B18 and Determination of the HLA-B18-Specific Binding Motif." *European Journal Immunology*. vol. 30, 2000, pp. 2281-2289.

Maaike E. Ressing, et al. "Human CTL Epitopes Encoded By Human Papillomavirus Type 16 E6 and E7 Identified Through In Vivo and In Vitro Immunogenicity Studies of HLA-A*0201-Binding Peptides[1]." *Journal of Immunology*. vol. 154, 1995, pp. 5934-5943.

Azoury-Ziadeh et al. "T-helper epitopes identified within the E6 transforming protein of cervical cancer-associated human Papillomavirus type 16." Viral Immunol. 12: 297-312, 1999.

* cited by examiner

*Primary Examiner*—Ali R. Salimi
(74) *Attorney, Agent, or Firm*—Morgan, Lewis & Bockius LLP

(57) ABSTRACT

The invention concerns a mixture of peptides derived from the E6 and/or E7 proteins of a papillomavirus involved in cervix of uterus cancer, such as HPV16, HPV18, HPV30, HPV31, HPV32, HPV33, HPV34, HPV35, HPV39, HPV40, HPV42, HPV43, HPV44, HPV45, HPV51, HPV52, HPV56, HPV57, and HPV58, for example, as well as its uses as medicine (in immunogenic compositions, capable of stimulating the production of anti-HPV T CD4+ lymphocytes in vivo and hence useful for vaccination against uterine of uterus cancer and in other cancers) or as diagnostic reagent of HPV-specific T lymphocytes, in particular for assessing the immune condition of patients. The invention also concerns a mixture of peptides derived from E6 and/or E7 proteins of a papillomavirus involved in benign skin lesions (for example warts), such as HPV10, HPV3 or HPV4 and its uses as medicine.

10 Claims, 1 Drawing Sheet

Figure 1:
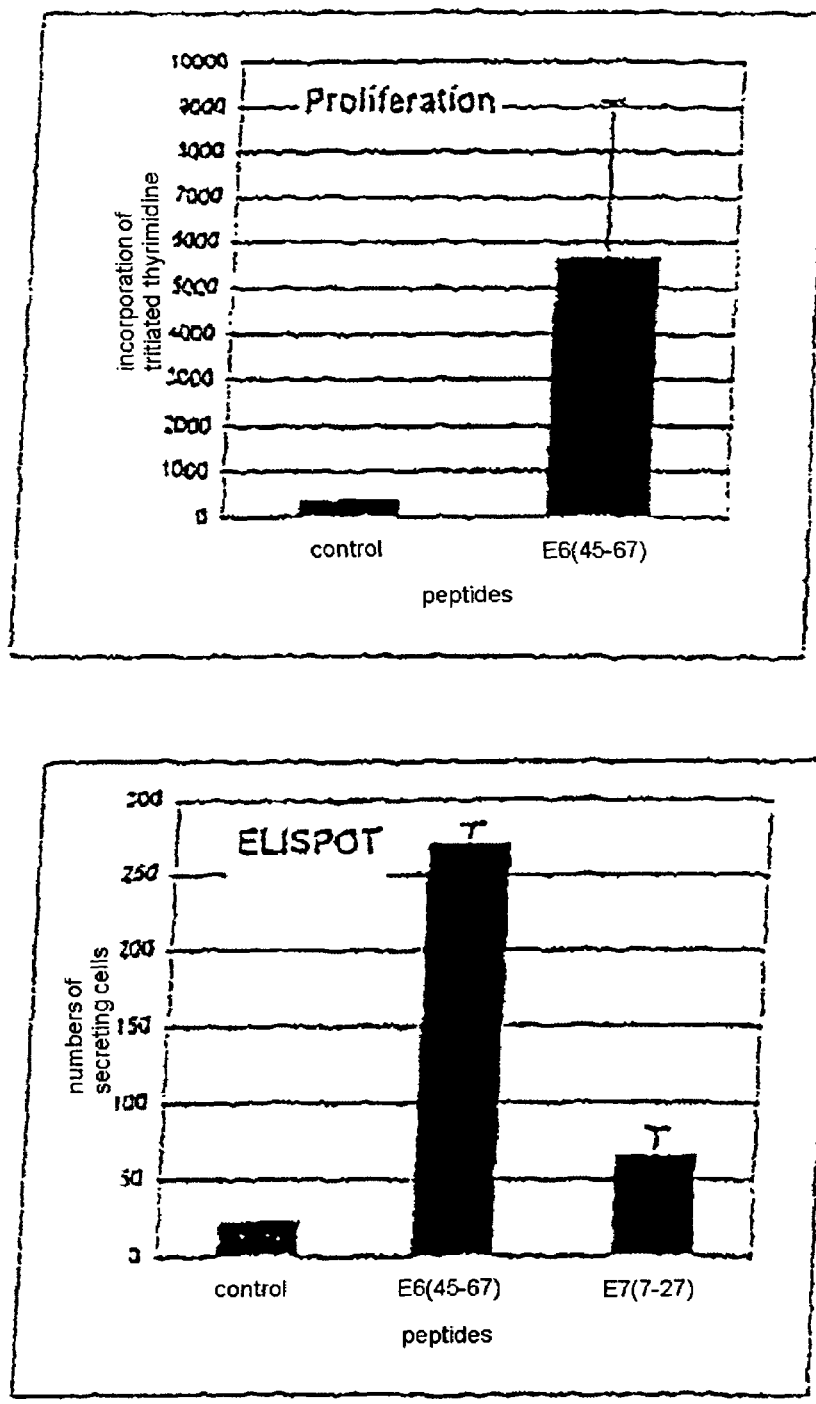

```
                              SEQUENCE LISTING

<160> NUMBER OF SEQ ID NOS: 63

<210> SEQ ID NO 1
<211> LENGTH: 13
<212> TYPE: PRT
<213> ORGANISM: artificial sequence
<220> FEATURE:
<223> OTHER INFORMATION: Description of the artificial sequence: peptide
      HA 306-318

<400> SEQUENCE: 1

Pro Lys Tyr Val Lys Gln Asn Thr Leu Lys Leu Ala Thr
 1               5                  10

<210> SEQ ID NO 2
<211> LENGTH: 15
<212> TYPE: PRT
<213> ORGANISM: artificial sequence
```

-continued

```
<220> FEATURE:
<223> OTHER INFORMATION: Description of the artificial sequence: peptide
      A3 152-166

<400> SEQUENCE: 2

Glu Ala Glu Gln Leu Arg Ala Tyr Leu Asp Gly Thr Gly Val Glu
 1               5                  10                  15

<210> SEQ ID NO 3
<211> LENGTH: 14
<212> TYPE: PRT
<213> ORGANISM: artificial sequence
<220> FEATURE:
<223> OTHER INFORMATION: Description of the artificial sequence: peptide
      MT 2-16

<400> SEQUENCE: 3

Ala Lys Thr Ile Ala Tyr Asp Glu Glu Ala Arg Gly Leu Glu
 1               5                  10

<210> SEQ ID NO 4
<211> LENGTH: 13
<212> TYPE: PRT
<213> ORGANISM: artificial sequence
<220> FEATURE:
<223> OTHER INFORMATION: Description of the artificial sequence: peptide
      YKL

<400> SEQUENCE: 4

Ala Ala Tyr Ala Ala Ala Lys Ala Ala Ala Leu Ala Ala
 1               5                  10

<210> SEQ ID NO 5
<211> LENGTH: 16
<212> TYPE: PRT
<213> ORGANISM: artificial sequence
<220> FEATURE:
<223> OTHER INFORMATION: Description of the artificial sequence: peptide
      B1 21-36

<400> SEQUENCE: 5

Thr Glu Arg Val Arg Leu Val Thr Arg His Ile Tyr Asn Arg Glu Glu
 1               5                  10                  15

<210> SEQ ID NO 6
<211> LENGTH: 20
<212> TYPE: PRT
<213> ORGANISM: artificial sequence
<220> FEATURE:
<223> OTHER INFORMATION: Description of the artificial sequence: peptide
      LOL 191-210

<400> SEQUENCE: 6

Glu Ser Trp Gly Ala Val Trp Arg Ile Asp Thr Pro Asp Lys Leu Thr
 1               5                  10                  15

Gly Pro Phe Thr
            20

<210> SEQ ID NO 7
<211> LENGTH: 14
<212> TYPE: PRT
<213> ORGANISM: artificial sequence
<220> FEATURE:
<223> OTHER INFORMATION: Description of the artificial sequence: peptide
      E2/E168

<400> SEQUENCE: 7
```

```
Ala Gly Asp Leu Leu Ala Ile Glu Thr Asp Lys Ala Thr Ile
 1               5                  10
```

```
<210> SEQ ID NO 8
<211> LENGTH: 21
<212> TYPE: PRT
<213> ORGANISM: artificial sequence
<220> FEATURE:
<223> OTHER INFORMATION: Description of the artificial sequence: peptide
      E6 14-34

<400> SEQUENCE: 8

Glu Arg Pro Arg Lys Leu Pro Gln Leu Cys Thr Glu Leu Gln Thr Thr
 1               5                  10                  15

Ile His Asp Ile Ile
             20
```

```
<210> SEQ ID NO 9
<211> LENGTH: 32
<212> TYPE: PRT
<213> ORGANISM: artificial sequence
<220> FEATURE:
<223> OTHER INFORMATION: Description of the artificial sequence: peptide
      E6 14-45

<400> SEQUENCE: 9

Glu Arg Pro Arg Lys Leu Pro Gln Leu Cys Thr Glu Leu Gln Thr Thr
 1               5                  10                  15

Ile His Asp Ile Ile Leu Glu Cys Val Tyr Cys Lys Gln Gln Leu Leu
             20                  25                  30
```

```
<210> SEQ ID NO 10
<211> LENGTH: 21
<212> TYPE: PRT
<213> ORGANISM: artificial sequence
<220> FEATURE:
<223> OTHER INFORMATION: Description of the artificial sequence: peptide
      E6 30-50

<400> SEQUENCE: 10

Ile His Asp Ile Ile Leu Glu Cys Val Tyr Cys Lys Gln Gln Leu Leu
 1               5                  10                  15

Arg Arg Glu Val Tyr
             20
```

```
<210> SEQ ID NO 11
<211> LENGTH: 20
<212> TYPE: PRT
<213> ORGANISM: artificial sequence
<220> FEATURE:
<223> OTHER INFORMATION: Description of the artificial sequence: peptide
      E6 61-80

<400> SEQUENCE: 11

Tyr Arg Asp Gly Asn Pro Tyr Ala Val Cys Asp Lys Cys Leu Lys Phe
 1               5                  10                  15

Tyr Ser Lys Ile
             20
```

```
<210> SEQ ID NO 12
<211> LENGTH: 20
<212> TYPE: PRT
<213> ORGANISM: artificial sequence
<220> FEATURE:
<223> OTHER INFORMATION: Description of the artificial sequence: peptide
      E6 76-95
```

```
<400> SEQUENCE: 12

Phe Tyr Ser Lys Ile Ser Glu Tyr Arg His Tyr Cys Tyr Ser Leu Tyr
 1               5                  10                  15

Gly Thr Thr Leu
            20

<210> SEQ ID NO 13
<211> LENGTH: 29
<212> TYPE: PRT
<213> ORGANISM: artificial sequence
<220> FEATURE:
<223> OTHER INFORMATION: Description of the artificial sequence: peptide
      E6 91-119

<400> SEQUENCE: 13

Tyr Gly Thr Thr Leu Glu Gln Gln Tyr Asn Lys Pro Leu Cys Asp Leu
 1               5                  10                  15

Leu Ile Arg Cys Ile Asn Cys Gln Lys Pro Leu Cys Pro
            20                  25

<210> SEQ ID NO 14
<211> LENGTH: 20
<212> TYPE: PRT
<213> ORGANISM: artificial sequence
<220> FEATURE:
<223> OTHER INFORMATION: Description of the artificial sequence: peptide
      E7 1-20

<400> SEQUENCE: 14

Met His Gly Asp Thr Pro Thr Leu His Glu Tyr Met Leu Asp Leu Gln
 1               5                  10                  15

Pro Glu Thr Thr
            20

<210> SEQ ID NO 15
<211> LENGTH: 21
<212> TYPE: PRT
<213> ORGANISM: artificial sequence
<220> FEATURE:
<223> OTHER INFORMATION: Description of the artificial sequence: peptide
      E7 7-27

<400> SEQUENCE: 15

Thr Leu His Glu Tyr Met Leu Asp Leu Gln Pro Glu Thr Thr Asp Leu
 1               5                  10                  15

Tyr Cys Tyr Glu Gln
            20

<210> SEQ ID NO 16
<211> LENGTH: 15
<212> TYPE: PRT
<213> ORGANISM: artificial sequence
<220> FEATURE:
<223> OTHER INFORMATION: Description of the artificial sequence: peptide
      E7 60-74

<400> SEQUENCE: 16

Lys Cys Asp Ser Thr Leu Arg Leu Cys Val Gln Ser Thr His Val
 1               5                  10                  15

<210> SEQ ID NO 17
<211> LENGTH: 23
<212> TYPE: PRT
<213> ORGANISM: artificial sequence
```

```
<220> FEATURE:
<223> OTHER INFORMATION: Description of the artificial sequence: peptide
      E7 65-87

<400> SEQUENCE: 17

Leu Arg Leu Cys Val Gln Ser Thr His Val Asp Ile Arg Thr Leu Glu
 1               5                  10                  15

Asp Leu Leu Met Gly Thr Leu
            20

<210> SEQ ID NO 18
<211> LENGTH: 21
<212> TYPE: PRT
<213> ORGANISM: artificial sequence
<220> FEATURE:
<223> OTHER INFORMATION: Description of the artificial sequence: peptide
      E7 78-98

<400> SEQUENCE: 18

Thr Leu Glu Asp Leu Leu Met Gly Thr Leu Gly Ile Val Cys Pro Ile
 1               5                  10                  15

Cys Ser Gln Lys Pro
            20

<210> SEQ ID NO 19
<211> LENGTH: 33
<212> TYPE: PRT
<213> ORGANISM: artificial sequence
<220> FEATURE:
<223> OTHER INFORMATION: Description of the artificial sequence: peptide
      E6 14-46

<400> SEQUENCE: 19

Glu Arg Pro Arg Lys Leu Pro Gln Leu Cys Thr Glu Leu Gln Thr Thr
 1               5                  10                  15

Ile His Asp Ile Ile Leu Glu Cys Val Tyr Cys Lys Gln Gln Leu Leu
            20                  25                  30

Arg

<210> SEQ ID NO 20
<211> LENGTH: 15
<212> TYPE: PRT
<213> ORGANISM: artificial sequence
<220> FEATURE:
<223> OTHER INFORMATION: Description of the artificial sequence: peptide
      E6 17-31

<400> SEQUENCE: 20

Arg Lys Leu Pro Gln Leu Cys Thr Glu Leu Gln Thr Thr Ile His
 1               5                  10                  15

<210> SEQ ID NO 21
<211> LENGTH: 15
<212> TYPE: PRT
<213> ORGANISM: artificial sequence
<220> FEATURE:
<223> OTHER INFORMATION: Description of the artificial sequence: peptide
      E6 20-34

<400> SEQUENCE: 21

Pro Gln Leu Cys Thr Glu Leu Gln Thr Thr Ile His Asp Ile Ile
 1               5                  10                  15

<210> SEQ ID NO 22
<211> LENGTH: 15
```

```
<212> TYPE: PRT
<213> ORGANISM: artificial sequence
<220> FEATURE:
<223> OTHER INFORMATION: Description of the artificial sequence: peptide
      E6 24-38

<400> SEQUENCE: 22

Thr Glu Leu Gln Thr Thr Ile His Asp Ile Ile Leu Glu Cys Val
 1               5                  10                  15

<210> SEQ ID NO 23
<211> LENGTH: 15
<212> TYPE: PRT
<213> ORGANISM: artificial sequence
<220> FEATURE:
<223> OTHER INFORMATION: Description of the artificial sequence: peptide
      E6 28-42

<400> SEQUENCE: 23

Thr Thr Ile His Asp Ile Ile Leu Glu Cys Val Tyr Cys Lys Gln
 1               5                  10                  15

<210> SEQ ID NO 24
<211> LENGTH: 15
<212> TYPE: PRT
<213> ORGANISM: artificial sequence
<220> FEATURE:
<223> OTHER INFORMATION: Description of the artificial sequence: peptide
      E6 31-45

<400> SEQUENCE: 24

His Asp Ile Ile Leu Glu Cys Val Tyr Cys Lys Gln Gln Leu Leu
 1               5                  10                  15

<210> SEQ ID NO 25
<211> LENGTH: 15
<212> TYPE: PRT
<213> ORGANISM: artificial sequence
<220> FEATURE:
<223> OTHER INFORMATION: Description of the artificial sequence: peptide
      E6 36-50

<400> SEQUENCE: 25

Glu Cys Val Tyr Cys Lys Gln Gln Leu Leu Arg Arg Glu Val Tyr
 1               5                  10                  15

<210> SEQ ID NO 26
<211> LENGTH: 22
<212> TYPE: PRT
<213> ORGANISM: artificial sequence
<220> FEATURE:
<223> OTHER INFORMATION: Description of the artificial sequence: peptide
      E6 45-67

<400> SEQUENCE: 26

Leu Arg Arg Glu Val Tyr Asp Phe Ala Arg Asp Leu Cys Ile Val Tyr
 1               5                  10                  15

Arg Asp Gly Asn Pro Tyr
            20

<210> SEQ ID NO 27
<211> LENGTH: 23
<212> TYPE: PRT
<213> ORGANISM: artificial sequence
<220> FEATURE:
<223> OTHER INFORMATION: Description of the artificial sequence: peptide
      E6 44-67
```

-continued

<400> SEQUENCE: 27

Leu Leu Arg Arg Glu Val Tyr Asp Phe Ala Arg Asp Leu Cys Ile Val
1               5                   10                  15

Tyr Arg Asp Gly Asn Pro Tyr
            20

<210> SEQ ID NO 28
<211> LENGTH: 15
<212> TYPE: PRT
<213> ORGANISM: artificial sequence
<220> FEATURE:
<223> OTHER INFORMATION: Description of the artificial sequence: peptide
      E6 42-56

<400> SEQUENCE: 28

Gln Gln Leu Leu Arg Arg Glu Val Tyr Asp Phe Ala Phe Arg Asp
1               5                   10                  15

<210> SEQ ID NO 29
<211> LENGTH: 15
<212> TYPE: PRT
<213> ORGANISM: artificial sequence
<220> FEATURE:
<223> OTHER INFORMATION: Description of the artificial sequence: peptide
      E6 50-64

<400> SEQUENCE: 29

Tyr Asp Phe Ala Phe Arg Asp Leu Cys Ile Val Tyr Arg Asp Gly
1               5                   10                  15

<210> SEQ ID NO 30
<211> LENGTH: 15
<212> TYPE: PRT
<213> ORGANISM: artificial sequence
<220> FEATURE:
<223> OTHER INFORMATION: Description of the artificial sequence: peptide
      E6 55-69

<400> SEQUENCE: 30

Arg Asp Leu Cys Ile Val Tyr Arg Asp Gly Asn Pro Tyr Ala Val
1               5                   10                  15

<210> SEQ ID NO 31
<211> LENGTH: 15
<212> TYPE: PRT
<213> ORGANISM: artificial sequence
<220> FEATURE:
<223> OTHER INFORMATION: Description of the artificial sequence: peptide
      E6 76-90

<400> SEQUENCE: 31

Phe Tyr Ser Lys Ile Ser Glu Tyr Arg His Tyr Cys Tyr Ser Leu
1               5                   10                  15

<210> SEQ ID NO 32
<211> LENGTH: 15
<212> TYPE: PRT
<213> ORGANISM: artificial sequence
<220> FEATURE:
<223> OTHER INFORMATION: Description of the artificial sequence: peptide
      E6 78-92

<400> SEQUENCE: 32

Ser Lys Ile Ser Glu Tyr Arg His Tyr Cys Tyr Ser Leu Tyr Gly
1               5                   10                  15

```
<210> SEQ ID NO 33
<211> LENGTH: 15
<212> TYPE: PRT
<213> ORGANISM: artificial sequence
<220> FEATURE:
<223> OTHER INFORMATION: Description of the artificial sequence: peptide
      E6 81-95

<400> SEQUENCE: 33

Ser Glu Tyr Arg His Tyr Cys Tyr Ser Leu Tyr Gly Thr Thr Leu
 1               5                  10                  15

<210> SEQ ID NO 34
<211> LENGTH: 15
<212> TYPE: PRT
<213> ORGANISM: artificial sequence
<220> FEATURE:
<223> OTHER INFORMATION: Description of the artificial sequence: peptide
      E6 84-98

<400> SEQUENCE: 34

Arg His Tyr Cys Tyr Ser Leu Tyr Gly Thr Thr Leu Glu Gln Gln
 1               5                  10                  15

<210> SEQ ID NO 35
<211> LENGTH: 20
<212> TYPE: PRT
<213> ORGANISM: artificial sequence
<220> FEATURE:
<223> OTHER INFORMATION: Description of the artificial sequence: peptide
      E6 91-110

<400> SEQUENCE: 35

Tyr Gly Thr Thr Leu Glu Gln Gln Tyr Asn Lys Pro Leu Cys Asp Leu
 1               5                  10                  15

Leu Ile Arg Cys
            20

<210> SEQ ID NO 36
<211> LENGTH: 15
<212> TYPE: PRT
<213> ORGANISM: artificial sequence
<220> FEATURE:
<223> OTHER INFORMATION: Description of the artificial sequence: peptide
      E6 89-103

<400> SEQUENCE: 36

Ser Leu Tyr Gly Thr Thr Leu Glu Gln Gln Tyr Asn Lys Pro Leu
 1               5                  10                  15

<210> SEQ ID NO 37
<211> LENGTH: 15
<212> TYPE: PRT
<213> ORGANISM: artificial sequence
<220> FEATURE:
<223> OTHER INFORMATION: Description of the artificial sequence: peptide
      E6 93-107

<400> SEQUENCE: 37

Thr Thr Leu Glu Gln Gln Tyr Asn Lys Pro Leu Cys Asp Leu Leu
 1               5                  10                  15

<210> SEQ ID NO 38
<211> LENGTH: 15
<212> TYPE: PRT
<213> ORGANISM: artificial sequence
<220> FEATURE:
<223> OTHER INFORMATION: Description of the artificial sequence: peptide
```

```
      E6 97-111

<400> SEQUENCE: 38

Gln Gln Tyr Asn Lys Pro Leu Cys Asp Leu Leu Ile Arg Cys Ile
 1               5                  10                  15

<210> SEQ ID NO 39
<211> LENGTH: 15
<212> TYPE: PRT
<213> ORGANISM: artificial sequence
<220> FEATURE:
<223> OTHER INFORMATION: Description of the artificial sequence: peptide
      E6 101-115

<400> SEQUENCE: 39

Lys Pro Leu Cys Asp Leu Leu Ile Arg Cys Ile Asn Cys Gln Lys
 1               5                  10                  15

<210> SEQ ID NO 40
<211> LENGTH: 23
<212> TYPE: PRT
<213> ORGANISM: artificial sequence
<220> FEATURE:
<223> OTHER INFORMATION: Description of the artificial sequence: peptide
      E6 118-140

<400> SEQUENCE: 40

Cys Pro Glu Glu Lys Gln Arg His Leu Asp Lys Lys Gln Arg Phe His
 1               5                  10                  15

Asn Ile Arg Gly Arg Trp Thr
            20

<210> SEQ ID NO 41
<211> LENGTH: 20
<212> TYPE: PRT
<213> ORGANISM: artificial sequence
<220> FEATURE:
<223> OTHER INFORMATION: Description of the artificial sequence: peptide
      E6 121-140

<400> SEQUENCE: 41

Glu Lys Gln Arg His Leu Asp Lys Lys Gln Arg Phe His Asn Ile Arg
 1               5                  10                  15

Gly Arg Trp Thr
            20

<210> SEQ ID NO 42
<211> LENGTH: 14
<212> TYPE: PRT
<213> ORGANISM: artificial sequence
<220> FEATURE:
<223> OTHER INFORMATION: Description of the artificial sequence: peptide
      E6 124-138

<400> SEQUENCE: 42

His Leu Asp Lys Lys Gln Arg Phe His Asn Ile Arg Gly Arg
 1               5                  10

<210> SEQ ID NO 43
<211> LENGTH: 15
<212> TYPE: PRT
<213> ORGANISM: artificial sequence
<220> FEATURE:
<223> OTHER INFORMATION: Description of the artificial sequence: peptide
      E6 130-144

<400> SEQUENCE: 43
```

```
Gln Arg Phe His Asn Ile Arg Gly Arg Trp Thr Gly Arg Cys Met
  1               5                  10                  15

<210> SEQ ID NO 44
<211> LENGTH: 24
<212> TYPE: PRT
<213> ORGANISM: artificial sequence
<220> FEATURE:
<223> OTHER INFORMATION: Description of the artificial sequence: peptide
      E6 135-158

<400> SEQUENCE: 44

Ile Arg Gly Arg Trp Thr Gly Arg Cys Met Ser Cys Cys Arg Ser Ser
  1               5                  10                  15

Arg Thr Arg Arg Glu Thr Gln Leu
              20

<210> SEQ ID NO 45
<211> LENGTH: 15
<212> TYPE: PRT
<213> ORGANISM: artificial sequence
<220> FEATURE:
<223> OTHER INFORMATION: Description of the artificial sequence: peptide
      E7 6-20

<400> SEQUENCE: 45

Pro Thr Leu His Glu Tyr Met Leu Asp Leu Gln Pro Glu Thr Thr
  1               5                  10                  15

<210> SEQ ID NO 46
<211> LENGTH: 15
<212> TYPE: PRT
<213> ORGANISM: artificial sequence
<220> FEATURE:
<223> OTHER INFORMATION: Description of the artificial sequence: peptide
      E7 9-23

<400> SEQUENCE: 46

His Glu Tyr Met Leu Asp Leu Gln Pro Glu Thr Thr Asp Leu Tyr
  1               5                  10                  15

<210> SEQ ID NO 47
<211> LENGTH: 15
<212> TYPE: PRT
<213> ORGANISM: artificial sequence
<220> FEATURE:
<223> OTHER INFORMATION: Description of the artificial sequence: peptide
      E7 13-27

<400> SEQUENCE: 47

Leu Asp Leu Gln Pro Glu Thr Thr Asp Leu Tyr Cys Tyr Glu Gln
  1               5                  10                  15

<210> SEQ ID NO 48
<211> LENGTH: 15
<212> TYPE: PRT
<213> ORGANISM: artificial sequence
<220> FEATURE:
<223> OTHER INFORMATION: Description of the artificial sequence: peptide
      E7 65-79

<400> SEQUENCE: 48

Leu Arg Leu Cys Val Gln Ser Thr His Val Asp Ile Arg Thr Leu
  1               5                  10                  15

<210> SEQ ID NO 49
```

```
<211> LENGTH: 15
<212> TYPE: PRT
<213> ORGANISM: artificial sequence
<220> FEATURE:
<223> OTHER INFORMATION: Description of the artificial sequence: peptide
      E7 67-81

<400> SEQUENCE: 49

Leu Cys Val Gln Ser Thr His Val Asp Ile Arg Thr Leu Glu Asp
 1               5                  10                  15

<210> SEQ ID NO 50
<211> LENGTH: 15
<212> TYPE: PRT
<213> ORGANISM: artificial sequence
<220> FEATURE:
<223> OTHER INFORMATION: Description of the artificial sequence: peptide
      E7 72-86

<400> SEQUENCE: 50

Thr His Val Asp Ile Arg Thr Leu Glu Asp Leu Leu Met Gly Thr
 1               5                  10                  15

<210> SEQ ID NO 51
<211> LENGTH: 15
<212> TYPE: PRT
<213> ORGANISM: artificial sequence
<220> FEATURE:
<223> OTHER INFORMATION: Description of the artificial sequence: peptide
      E7 77-91

<400> SEQUENCE: 51

Arg Thr Leu Glu Asp Leu Leu Met Gly Thr Leu Gly Ile Val Cys
 1               5                  10                  15

<210> SEQ ID NO 52
<211> LENGTH: 15
<212> TYPE: PRT
<213> ORGANISM: artificial sequence
<220> FEATURE:
<223> OTHER INFORMATION: Description of the artificial sequence: peptide
      E7 84-98

<400> SEQUENCE: 52

Met Gly Thr Leu Gly Ile Val Cys Pro Ile Cys Ser Gln Lys Pro
 1               5                  10                  15

<210> SEQ ID NO 53
<211> LENGTH: 30
<212> TYPE: PRT
<213> ORGANISM: artificial sequence
<220> FEATURE:
<223> OTHER INFORMATION: Description of the artificial sequence: peptide
      E6 15-44

<400> SEQUENCE: 53

Arg Pro Arg Lys Leu Pro Gln Leu Cys Thr Glu Leu Gln Thr Thr Ile
 1               5                  10                  15
His Asp Ile Ile Leu Glu Cys Val Tyr Cys Lys Gln Gln Leu
            20                  25                  30

<210> SEQ ID NO 54
<211> LENGTH: 21
<212> TYPE: PRT
<213> ORGANISM: artificial sequence
<220> FEATURE:
<223> OTHER INFORMATION: Description of the artificial sequence: peptide
      E6 46-67
```

```
<400> SEQUENCE: 54

Arg Arg Glu Val Tyr Asp Phe Ala Arg Asp Leu Cys Ile Val Tyr Arg
  1               5                  10                  15

Asp Gly Asn Pro Tyr
             20

<210> SEQ ID NO 55
<211> LENGTH: 29
<212> TYPE: PRT
<213> ORGANISM: artificial sequence
<220> FEATURE:
<223> OTHER INFORMATION: Description of the artificial sequence: peptide
      E6 80-108

<400> SEQUENCE: 55

Ile Ser Glu Tyr Arg His Tyr Cys Tyr Ser Leu Tyr Gly Thr Thr Leu
  1               5                  10                  15

Glu Gln Gln Tyr Asn Lys Pro Leu Cys Asp Leu Leu Ile
             20                  25

<210> SEQ ID NO 56
<211> LENGTH: 22
<212> TYPE: PRT
<213> ORGANISM: artificial sequence
<220> FEATURE:
<223> OTHER INFORMATION: Description of the artificial sequence: peptide
      E6 118-139

<400> SEQUENCE: 56

Cys Pro Glu Glu Lys Gln Arg His Leu Asp Lys Lys Gln Arg Phe His
  1               5                  10                  15

Asn Ile Arg Gly Arg Trp
             20

<210> SEQ ID NO 57
<211> LENGTH: 23
<212> TYPE: PRT
<213> ORGANISM: artificial sequence
<220> FEATURE:
<223> OTHER INFORMATION: Description of the artificial sequence: peptide
      E7 3-25

<400> SEQUENCE: 57

Gly Asp Thr Pro Thr Leu His Glu Tyr Met Leu Asp Leu Gln Pro Glu
  1               5                  10                  15

Thr Thr Asp Leu Tyr Cys Tyr
             20

<210> SEQ ID NO 58
<211> LENGTH: 19
<212> TYPE: PRT
<213> ORGANISM: artificial sequence
<220> FEATURE:
<223> OTHER INFORMATION: Description of the artificial sequence: peptide
      E7 79-97

<400> SEQUENCE: 58

Leu Glu Asp Leu Leu Met Gly Thr Leu Gly Ile Val Cys Pro Ile Cys
  1               5                  10                  15

Ser Gln Lys

<210> SEQ ID NO 59
<211> LENGTH: 22
```

```
<212> TYPE: PRT
<213> ORGANISM: artificial sequence
<220> FEATURE:
<223> OTHER INFORMATION: Description of the artificial sequence: peptide
      E6 1-22

<400> SEQUENCE: 59

Met His Gln Lys Arg Thr Ala Met Phe Gln Asp Pro Gln Glu Arg Pro
 1               5                  10                  15

Arg Lys Leu Pro Gln Leu
             20

<210> SEQ ID NO 60
<211> LENGTH: 22
<212> TYPE: PRT
<213> ORGANISM: artificial sequence
<220> FEATURE:
<223> OTHER INFORMATION: Description of the artificial sequence: peptide
      E6 105-126

<400> SEQUENCE: 60

Asp Leu Leu Ile Arg Cys Ile Asn Cys Gln Lys Pro Leu Cys Pro Glu
 1               5                  10                  15

Glu Lys Gln Arg His Leu
             20

<210> SEQ ID NO 61
<211> LENGTH: 20
<212> TYPE: PRT
<213> ORGANISM: artificial sequence
<220> FEATURE:
<223> OTHER INFORMATION: Description of the artificial sequence: peptide
      E7 21-40

<400> SEQUENCE: 61

Asp Leu Tyr Cys Tyr Glu Gln Leu Asn Asp Ser Ser Glu Glu Glu Asp
 1               5                  10                  15

Glu Ile Asp Gly
             20

<210> SEQ ID NO 62
<211> LENGTH: 21
<212> TYPE: PRT
<213> ORGANISM: artificial sequence
<220> FEATURE:
<223> OTHER INFORMATION: Description of the artificial sequence: peptide
      E7 35-55

<400> SEQUENCE: 62

Glu Asp Glu Ile Asp Gly Pro Ala Gly Gln Ala Glu Pro Asp Arg Ala
 1               5                  10                  15

His Tyr Asn Ile Val
             20

<210> SEQ ID NO 63
<211> LENGTH: 15
<212> TYPE: PRT
<213> ORGANISM: artificial sequence
<220> FEATURE:
<223> OTHER INFORMATION: Description of the artificial sequence: peptide
      E7 43-57

<400> SEQUENCE: 63

Gly Gln Ala Glu Pro Asp Arg Ala His Tyr Asn Ile Val Thr Phe
 1               5                  10                  15
```

MIXTURE OF PEPTIDES DERIVED FROM E6 AND/OR E7 PAPILLOMAVIRUS PROTEINS AND USES THEREOF

The present invention relates to a mixture of peptides derived from the E6 and/or E7 proteins of a papillomavirus involved in cervical cancer, such as HPV16 (papillomavirus genotype 16), HPV18, HPV30, HPV31, HPV32, HPV33, HPV34, HPV35, HPV39, HPV40, HPV42, HPV43, HPV44, HPV45, HPV51, HPV52, HPV56, HPV57 and HPV58, for example, and also to uses thereof as a medicinal product (in immunogenic compositions capable of stimulating the production of anti-HPV CD4+ T lymphocytes in vivo, and therefore useful for immunization against cervical cancer and in other cancers) or as a reagent for diagnosing T lymphocytes specific for an HPV, in particular for evaluating the immune state of patients.

The present invention also relates to a mixture of peptides derived from the E6 and/or E7 proteins of a papillomavirus involved in benign lesions of the skin (warts for example), such as HPV10, HPV3 and HPV4, and to uses thereof as a medicinal product.

Human papillomaviruses (HPVs) induce benign lesions of the skin and of the mucous membranes, but are also involved in the induction of malignant lesions. They have mainly been involved in cervical cancer, which constitutes, throughout the world, the second most common cause of death from cancer in women.

They also contribute to the development of certain cancers of the penis, of the anus and of the oropharynx. The DNA of these viruses is in fact very commonly detected by PCR in biopsies from patients (1). 20 to 50% of cancers of the penis and 70% of cancers of the anus reveal the presence of HPV DNA.

There are in fact more than 100 different genotypes of papillomavirus, each having its own pathogenicity. The association between infection with HPV and cervical cancer in fact varies according to genotypes. The low or zero malignant transformation-risk strains such as the HPV6 and HPV11 viruses are distinguished from the high-risk strains such as HPV16 and HPV18 viruses. Whatever the country, HPV16 is found in 40 to 60% of cervical cancers, whereas HPV18 is present in 10 to 20% of cases. Most of the other patients suffering from cervical cancer are infected with HPV31, HPV33 or HPV45.

For 1% of patients, no papillomavirus DNA is detected.

Experiments consisting of in vitro immortalization of keratinocytes with HPV DNA have revealed that two genes (E6 and E7) are mainly responsible for the cell transformation. In these experiments, the DNA derived from high-risk viral strains is capable of transforming the cells, whereas the low-risk strains are not capable of doing this. The E6 protein binds to p53, which has tumor-suppressing activity, and induces its degradation. The E7 protein binds to the pRb protein, which also has tumor-suppressing activity. These activities are higher for the E6 and E7 proteins of high-risk strains than for the low-risk strains. In addition, the pRb and p53 genes are mutated and inactive in cervical cell lines which are not infected with HPV, whereas this is not the case in infected lines. All of these observations strongly suggest that the E6 and E7 proteins are key components of HPV infection and of the induction of cancerous states.

In the absence of antiviral treatments specific for HPV infections, the development of anti-HPV vaccines constitutes one of the promising approaches for combating the forms of cancer induced by these viruses.

The use of attenuated or inactivated forms of viruses is, however, difficult to apply due, firstly, to the current lack of means for producing the virus and, secondly, to the presence in its genome of transforming genes.

An approach based on peptides or subunits therefore appears to be very advantageous. In particular, it is known that suitably chosen peptides are capable of recruiting both cytotoxic T lymphocytes (CTLs) and helper T lymphocytes of the Th1 type directed specifically against the transformed cells.

In this context, the E6 and E7 proteins constitute preferred targets since they contribute directly to the cancerization of cells, and their early expression after infection persists in the transformed cell.

Various immunization strategies using peptides derived from these two proteins have thus been recommended.

These strategies are based on the fact that CD4+ T lymphocytes play a major role in establishing the immune responses and in particular of the CTLs. Recent studies have shown that they are involved, via CD40 molecules, in the activation of dendritic antigen-presenting cells which are required for stimulation of the specific CTLs (J. P. Ridge et al., *Nature*, 1998, 393, 474; S. P. Schoenberger et al., *Nature*, 1998, 393, 480; S, R. Bennett et al., *Nature*, 1998, 393, 478; R. E M. Toes et al., *Semin. Immunol.*, 1998, 10, 443).

The activation of the CD4+ T lymphocytes takes place through the presentation of the viral peptides by the HLA II molecules carried by the antigen-presenting cells (APCs). These peptides, called T epitopes, result from the proteolytic degradation of the viral antigens by the APC. They are variable in length, generally from 13 to 25 amino acids, and have a sequence which makes them capable of binding to the HLA II molecules.

It is now established that a peptide, T epitope, is capable, to the same extent as the native antigen, of stimulating, in vitro, CD4+ T lymphocytes which are specific for it, or of recruiting them in vivo.

T epitopes are therefore sufficient to induce a CD4+ response. However, one of the major problems which limits the use of these peptides is that their sequence varies from one individual to another, due to the polymorphism of HLA II molecules, which are heterodimers expressed on the antigen-presenting cells (APCs) and which present to the CD4+ T lymphocytes the T epitopes of said antigens. These molecules are capable of binding a considerable repertoire of peptides having very different sequences, which allows them to present to the T cells several peptides per antigen.

Four different types of HLA II molecule exist per individual: 2 HLA-DR, 1 HLA-DQ and 1 HLA-DP; the HLA-DR molecule, the β-chain of which is encoded by the DRB1 gene (1st gene), is the most highly expressed. There are currently listed more than 200 different alleles for DRB1, which define various antigens or types, as summarized in table I below.

TABLE 1

Molecules expressed by various HLA-DRB1 alleles

| Antigen | Allele | Alias |
|---|---|---|
| DR1 | DRB1*0101 | DR1 |
| DR3 | DRB1*0301 | DR3w17 |
| DR4 | DRB1*0401 | DR4w4 |
|  | DRB1*0405 | DR4w15 |
| DR7 | DRB1*0701 | DR7 |
| DR8 | DRB1*0802 | DR8w2 |
| DR9 | DRB1*0901 | DR9 |
| DR11 | DRB1*1101 | DR5w11 |

TABLE 1-continued

Molecules expressed by various HLA-DRB1 alleles

| Antigen | Allele | Alias |
|---|---|---|
| DR12 | DRB1*1201 | DR5w12 |
| DR13 | DRB1*1301 | |
| | DRB1*1302 | DR6w19 |
| DR15 | DRB1*1501 | DR2w2b |

Each allele has its own binding properties; the wide specificity of the HLA II molecules and the existence of several isoforms and of a polymorphism mean that each individual recognizes, in an antigen, a set of peptides the nature of which depends on the HLA II molecules which characterize it. Since a large number of HLA II alleles exist, a large number of T epitopes, specific for each allele, therefore exist for a given antigen.

In addition, the distribution of the alleles in a given population is not homogeneous: for example, in the French population, which corresponds to a mainly Caucasian population, only 7 alleles of the DRB1 locus exceed 5%; these are the alleles: DRB1*0101, DRB1*0301, DRB1*0401, DRB1*0701, DRB1*1101, DRB1*1301 and DRB1*1501, which represent 64% of the population (4). These same alleles are also in the majority in other European populations, where their frequency ranges from 53% (Spain) to 82% (Denmark), and also in North America (55-58%).

The HLA-DRB3, -DRB4 and -DRB5 molecules (2nd gene), which are HLA-DR molecules wherein the β-chain is not encoded by the DRB1 gene, are also present with high allelic frequencies in the various Caucasian populations: 9.2% for DRB3*0101 (B3), 28.4% for DRB4*0101 (B4) and 7.9% for DRB5*0101 (B5). They therefore cover, by themselves, 45% of the allelic frequency in Caucasian populations.

The peptides present in a peptide sequence and which bind all these alleles include the T epitopes of the majority of the Caucasian population.

One of the most commonly used means for defining helper CD4+ T epitopes is to measure the ability of the peptides to cause proliferation of the mononuclear cells of individuals having been in contact with the antigen under consideration.

A certain number of documents propose a selection of epitopes derived from the E6 or E7 proteins of HPV16, which can be used to produce a vaccine:

International application WO 00/14244 (Connaught Laboratories Ltd) recommends, to obtain a specific immunity without producing any risks of oncogenic transformation, the use of constructs (vectors) wherein a certain number of T epitopes derived both from E6 and from E7 are linked together. More precisely, the antigens can be in the form of whole proteins or of T epitopes. For example, the T epitope of the E6 protein is preferably the epitope corresponding to positions 29-38 of said protein and the preferred epitopes of the E7 protein are those corresponding respectively to positions: 11-20, 49-57, 82-90, 86-93; the use of an E7 protein detoxified by deletion of the Rb protein-binding site is also envisioned.

Application EP 0 451 550 (Behringwerke) describes seroactive epitopes and in particular epitopes derived from the E6 protein or from the E7 protein of HPV16, and also a vaccine containing one or more of said epitopes.

Patent EP 0 561 885 (University of Queensland and CSL Ltd) describes a subunit vaccine against the HPV16 papillomavirus, which comprises the sequence DRAHYNI of the E7 protein (positions 48-54), considered to induce an immune response significantly greater than other epitopes.

Patent application 0 386 734 (Behringwerke) describes two dominant immunogenic regions in the E7 protein of HPV16, corresponding respectively to positions 12-27 and 36-52, and their use in reagents for detection.

Luxton et al. have emphasized the importance of cellular immunity in the control of genital infections with HPV and have, consequently, studied the proliferative T response to HPV infections; insofar as immunization of mice with peptides derived from the E6 and E7 proteins of HPV16 protects against a virulent challenge consisting of HPV16-transformed cancerous cells, they have in particular shown the advantage of the E7 protein of HPV16 and have sought to identify T epitopes in this protein. To do this, they have produced synthetic peptides of 15 amino acids, the sequence of which overlaps by 5 amino acids, so as to obtain a series of peptides representing the entire sequence of the E7 protein. They have shown that the proliferative T response depends on the state of the patient and that, in asymptomatic individuals, the peptides located in the N- and C-terminal regions (peptides 1-34 and 70-98) induce an immunological response, whereas this is not the case in the patients exhibiting cervical dysplasia. They have mainly shown that the E7 peptide 80-94 of the HPV16 genotype causes the cells of 6 individuals out of the 7 tested to proliferate (*J. Gen. Virol.*, 1996, 77, 1585) (see table II below).

G. Strang et al. have defined four T epitopes of HPV16, one of which is present in E6 (*J. Gen. Virol.*, 1990, 71, 423).

A. Altmann et al. have isolated E7-specific T lymphocyte lines from two patients and characterized the peptides recognized (*Eur. J. Cancer*, 1992, 28, 326). The study was carried out with synthetic peptides of 14 amino acids, the sequence of which overlaps by 10 amino acids, so as to obtain a series of peptides representing the entire sequence of the E7 protein.

T. Tsukui et al. has studied the secretion of IL2 by cells in the blood, in 140 HPV16+ patients having various stages of lesion (*Cancer Res.*, 1996, 56, 3967).

M. Nakagawa et al. have mainly observed that peptide 24-45 of E6 of the HPV16 genotype causes proliferation of the cells of 13 individuals out of 63 tested (*Immunol.*, 1996, 3, 205). They have also studied the responses observed with the E7 protein and has shown that little response is observed with this protein.

A. S. Kadish et al. has studied the proliferative response of the cells of HPV16+ patients to E6 and E7 peptides (*Cancer Inst.*, 1997, 89, 1285).

T. D. de Gruijl et al. have studied the proliferation of cells from patients infected with HPV and have observed that, among the peptides covering the sequence of the E7 protein of the HPV16 virus, peptide 67-98 stimulates the cells of a majority of patients (*Cancer Res.*, 1998, 58, 1700).

All the E6 and E7 sequences identified as being T epitopes in the patients studied are illustrated in table II.

TABLE II

| Documents | HPV16 peptides (positions) | Properties |
|---|---|---|
| WO 00/14244 | E6: 29-38<br>E7: 11-20, 49-57, 82-90, 86-93 | |
| EP 0 451 550 | E6: 7-37<br>E7: 6-26, 9-19, 7-21, 10-23, 36-52, 40-54 | |
| EP 0 561 885 | E7: 48-54, 44-54, 44-62, 44-57, 44-56, 44-60, 44-48, 38-41, 10-14, 11-14 | |
| EP 0 375 555 | E7: 45-58 | |
| EP 0 386 734 | E7: 12-27, 12-23, 12-20, 12-19 and 36-52 | |
| Strang et al. (14) | E6: 42-57 | Recognized by DR7-restricted clone |
| Altmann et al. (15) | E7: 5-18 | Recognized by line from a DR1 DR11 patient |
| | E7: 17-34 | Recognized by line from a DR4 DR13 patient |
| | E7: 69-82 | Recognized by clone from a DR4 DR13 patient |
| Tsukui et al. (17) | | Secretion of IL2 (activation of cells) by patients |
| | E6: 1-45 | 0/140 |
| | E6: 59-112 | 6/140 |
| | E6: 111-158 | 11/140 |
| | E7: 1-35 | 3/140 |
| | E7: 27-60 | 4/140 |
| | E7: 51-98 | 7/140 |
| Luxton et al. (16) | | Proliferation of cells from patients (CIN or normal) |
| | E7: 1-14 | 0/31 CIN and 1/15 normal |
| | E7: 10-24 | 0/31 CIN and 3/15 normal |
| | E7: 20-34 | 0/31 CIN and 0/15 normal |
| | E7: 25-49 | 3/31 CIN |
| | E7: 30-44 | 2/31 normal |
| | E7: 40-54 | 0 CIN and 0 normal |
| | E7: 45-64 | 2/31 CIN and 1/15 normal |
| | E7: 55-74 | 2/31 CIN and 1/15 normal |
| | E7: 70-98 | 4/31 CIN and 7/15 normal |
| Nakagawa et al. (18) | | Proliferation of cells from patients (CIN or normal) |
| | E6: 4-29 | 3/22 CIN and 12/65 normal |
| | E6: 24-45 | 1/22 CIN and 15/65 normal |
| | E6: 109-122 | 1/22 CIN and 8/65 normal |
| | E7: 21-30 | 0/22 CIN and 5/65 normal |
| | E7: 44-57 | 3/22 CIN and 9/65 normal |
| | E7: 62-79 | 3/22 CIN and 10/65 normal |
| Kadish et al. (19) | | Proliferation of cells from patients (CIN or normal) |
| | E6: 1-31 | 17/48 |
| | E6: 22-51 | 17/46 |
| | E6: 42-71 | 8/43 |
| | E6: 62-91 | 0/30 |
| | E6: 82-111 | 5/34 |
| | E6: 102-131 | 14/43 |
| | E6: 122-151 | 19/48 |
| | E6: 142-159 | 17/49 |
| | E6: 17-31 | 12/23 |
| | E6: 117-131 | 12/23 |
| | E6: 137-151 | 9/23 |
| | E7: 62-80 | 11/35 |
| | E7: 72-97 | 19/48 |
| De Gruijl et al. (20) | E7: 1-32 | 8/28 |
| | E7: 19-56 | 10/28 |
| | E7: 43-80 | 10/28 |
| | E7: 67-98 | 17/28 |

Considerable differences are observed between the studies, reflecting the relative imprecision of this approach. It is in fact difficult, in view of the diversity of the responses observed, to define T epitope sequences for the entire population. These sequences are adapted only to the patients involved in these studies. These differences in response can be explained, firstly, by the representativeness of the samples, which is not evaluated. In particular, in the studies where the patients are not typed for their HLA molecules, no one knows whether the various alleles are represented according to the frequencies in the general population. A response, common to many patients, to a particular peptide may therefore result from a bias in the sampling and not from the effective ability of a peptide to be recognized by all the patients. Furthermore, in the case of infection with HPV, the persistence of the antigen may induce a state of immune tolerance against the T epitopes of the virus, those best recognized by the T cells, as has been shown in a mouse model transgenic for the E7 protein of HPV (T. Doan et al., *J. Virol.*, 1999, 73, 6166). In this respect, it may be noted that the response is often weaker in the patients who have eliminated the virus compared to the infected patients (T. Tsukui et al., 1996, mentioned above). In this context, the most advantageous epitopes might have disappeared from the immune response, which would be maintained for less stimulatory determinants but which would not succeed in eliminating the virus.

These proliferation assays are therefore insufficient to define sequences suitable for the entire population.

Thus, it emerges from the various studies that the peptides that helper T lymphocytes recognize are difficult to define due to the polymorphism of the HLA II molecules.

In addition, to date, immunization trials in women to induce anti-HPV immunity have not made it possible to obtain clinically satisfactory results. Eight patients suffering from cervical cancer were immunized with a dose of vaccinia virus recombined with the genes encoding the E6 and E7 proteins (L. K. Borysiewicz et al., *Lancet.*, 1996, 347, 1523). A cytotoxic response was detected only transiently and in only one patient.

The results obtained with peptides have also not been very conclusive, with zero clinical effectiveness. M. E. Ressing et al. (*J. Immunother.*, 2000, 23, 255) and W. J. Van Driel et al. (*Eur. J. Cancer*, 1999, 35, 946) have used a combination of two HPV peptides and a helper peptide which is universal but not specific for the virus. No cytotoxic response was induced. It is probable that the lack of response is due to the inability of the constructs to induce stimulation of both the HPV-specific helper CD4+ T lymphocytes and the CD8+ lymphocytes.

Consequently, all the peptides proposed to date correspond to T epitopes, which are specific only for particular individuals; in fact, an inter-individual variability in T epitopes exists which makes it difficult to choose molecules suitable for mass immunization against HPV16; consequently, the peptides described above are not suitable for the preparation of an immunogenic and immunizing composition capable of stimulating anti-HPV16 CD4+ T lymphocytes and generating a protective immune response, regardless of the individual to be protected, since they do not stimulate a protective CD4+ T response in all the individuals to be treated.

For this reason, the inventors gave themselves the aim of providing a set of peptides capable of being incorporated into an immunogenic composition and of stimulating anti-HPV CD4+ T lymphocytes, in the majority of European or North American Caucasian individuals, so as to effectively induce a specific proliferative response against components of the virus.

Such a set has the property of being effective in a large number of individuals, whereas the peptides of the prior art are active in some individuals and are inactive in most of the other individuals, because the latter do not recognize the E6 and E7 proteins of HPV16 via the same determinants.

To do this, the inventors have selected peptides derived from the E6 and E7 proteins of one of the abovementioned HPVs, in particular of HPV16, restricted with respect to the HLA II molecules predominant in Caucasian populations, and have found that, in combination, the peptides selected effectively induce an immunogenic and protective response in a large number of individuals.

Consequently, a subject of the present invention is a mixture of peptides derived from an E6 protein and/or from an E7 protein of an HPV involved in cervical cancer or benign lesions of the skin, characterized in that each of the peptides included in said mixture binds to at least one HLA-DRB1 (1st gene) molecule the frequency of which is greater than 5% in the Caucasian population and, optionally, to at least one HLA-DRB3, HLA-DRB4 or HLA-DRB5 (2nd gene) molecule, with a binding activity <1 000 nM, preferably <800 nM, said mixture of peptides binding at least eight HLA class II molecules, the frequency of which is greater than 5% in the Caucasian population, encoded by the alleles selected from the group consisting of the alleles HLA DRB1*0101, DRB1*0301, DRB1*0401, DRB1*0701, DRB1*1101, DRB1*1301 and DRB1*1501 (DR1, DR3, DR4, DR7, DR11, DR13 and DR15 molecules) (1st gene) and the alleles DRB3*0101, DRB4*0101 and DRB5*0101 (B3, B4 and B5) (2nd gene).

Such a mixture of peptides makes it possible to obtain, surprisingly, a proliferative CD4+ T response (stimulation of CD4+ T lymphocytes) and also stimulation of the CTL response, in a great majority of the Caucasian population to be protected and whatever the HPV concerned; it may therefore be considered that such a mixture constitutes a first step toward a "universal" immunogenic composition which can be used in a vaccine.

According to an advantageous embodiment of said mixture, the peptides derived from an E6 protein of HPV are derived from HPV16 and are selected from the group consisting of:

(a) a peptide included between positions 14 and 16, selected from the group consisting of the peptide corresponding to positions 14-34 and the peptide corresponding to positions 14-46 (SEQ ID Nos. 8, 19), (b) the peptide corresponding to positions 30-50 (SEQ ID No. 10), (c) a peptide included between positions 44 and 67, selected from the group consisting of the peptide corresponding to positions 45-67 and the peptide corresponding to positions 44-67 (SEQ ID Nos. 26, 27), (d) the peptide corresponding to positions 61-80 (SEQ ID No. 11), (e) a peptide included between positions 76 and 119, selected from the group consisting of the peptide corresponding to positions 76-95, the peptide corresponding to positions 91-110 and the peptide corresponding to positions 91-119 (SEQ ID Nos. 12, 35, 13), (f) a peptide included between positions 118-140, selected from the group consisting of the peptide corresponding to positions 118-140 and the peptide corresponding to positions 121-140 (SEQ ID Nos. 40, 41), (g) the peptide corresponding to positions 135-158 (SEQ ID No. 44), of the E6 protein of HPV16, and (h) the peptides, preferably of 15 to 20 amino acids, exhibiting an amino acid sequence having at least 60% identity or at least 80% similarity, and preferably at least 70% identity or at least 99% similarity, with the peptides defined in (a)-(g), said peptides being identical in size, or included in the peptides defined in (a)-(g) or else completely or partially overlapping these peptides, with the exclusion of the peptides corresponding to positions 15-44, 46-67, 80-108 and 118-139 (SEQ ID Nos. 53-56) of the E6 protein of HPV16.

The identity of a sequence with respect to a reference sequence is assessed as a function of the percentage of amino acid residues which are identical, when the two sequences are aligned so that they correspond to one another to a maximum.

A peptide having an amino acid sequence having at least X % identity with a reference sequence comprising Y amino acids is defined, in the present invention, as a peptide the sequence of which can include up to Y-X' alterations per Y amino acids of the reference sequence and reformulated for a sequence of 100 amino acids.

The similarity of a sequence with respect to a reference sequence is assessed as a function of the percentage of amino acid residues which are identical or which differ by conservative substitutions, when these two sequences are aligned so that they correspond to one another to a maximum. For the purpose of the present invention, the term "conservative substitution" is intended to mean the substitution of an amino acid with another which exhibits similar chemical properties (size, charge or polarity), which generally does not modify the functional properties of the peptide.

Advantageously, the peptides derived from an E6 protein of HPV of said mixture, as defined in (h), are selected from the group consisting of:

the peptides of 15 amino acids included in the peptide corresponding to positions 14-34 or overlapping this peptide, chosen from the peptides corresponding respectively to positions 20-34, 24-38 and 28-42 (SEQ ID Nos. 21-23), the peptides of 15 amino acids included in the peptide corresponding to positions 30-50 or overlapping this peptide, chosen from the peptides corresponding respectively to positions 31-45 and 36-50 (SEQ ID Nos. 24-25);

the peptides of 15 amino acids included in the peptide corresponding to positions 45-67 or overlapping this peptide, chosen from the peptides corresponding respectively to positions 42-56, 50-64 and 55-69 (SEQ ID Nos. 28-30);

the peptides of 15 to 17 amino acids included in the peptide corresponding to positions 76-95 or overlapping this peptide, chosen from the peptides corresponding respectively to positions 76-90, 78-92, 81-95 and 84-98 (SEQ ID Nos. 31-34);

the peptides of 15 amino acids included in the peptide corresponding to positions 91-110 or overlapping this peptide, chosen from the peptides corresponding, respectively, to positions 89-103, 93-107, 97-111 and 101-115 (SEQ ID Nos. 36-39);

the peptides of 15 amino acids included in the peptide corresponding to positions 121-140 or overlapping this peptide, chosen from the peptides corresponding respectively to positions 124-138 and 130-144 (SEQ ID Nos. 42-43).

According to another advantageous embodiment of said mixture, the peptides derived from an E7 protein are derived from HPV16 and are selected from the group consisting of the peptide corresponding to positions 1-20, the peptide corresponding to positions 7-27, the peptide corresponding to positions 65-87 and the peptide corresponding to positions 78-98 of said E7 protein of HPV16 (SEQ ID Nos. 14, 15, 17, 18) and the peptides, preferably of 15 to 20 amino acids, exhibiting an amino acid sequence having at least 60% identity or at least 80% similarity, and preferably at least 70% identity or at least 99% similarity, with the peptides as defined above, said peptides being identical in size, or included in the peptides as defined above or else overlapping these peptides, with the exclusion of the peptides corresponding to positions 3-25 and 79-97 of the E7 protein of HPV16 (SEQ ID Nos. 57, 58).

Advantageously, the peptides derived from an E7 protein of said mixture, included in the peptides (SEQ ID Nos. 14, 15, 17, 18) as defined above or else overlapping these peptides, are selected from the group consisting of the peptides corresponding respectively to positions 6-20, 9-23, 13-27, 65-79, 67-81, 72-86, 77-91 and 84-98 of the E7 protein of HPV16 (SEQ ID Nos. 45-52).

Particularly advantageously, said mixture of peptides according to the invention is selected from the group consisting of the following mixtures:

- a mixture of peptides derived from the E6 protein of HPV16, comprising: the peptide corresponding to positions 14-34 or to positions 14-46, the peptide corresponding to positions 30-50 and the peptide corresponding to positions 44-67 or to positions 45-67;
- a mixture of peptides derived from the E6 protein of HPV16, comprising: the peptide corresponding to positions 61-80, the peptide corresponding to positions 76-95 and the peptide corresponding to positions 91-119;
- a mixture of peptides derived from the E7 protein of HPV16, comprising: the peptide corresponding to positions 1-20 and the peptide corresponding to positions 7-27;
- a mixture of peptides derived from the E7 protein of HPV16, comprising: the peptide corresponding to positions 65-87 and the peptide corresponding to positions 78-98;
- and the mixtures comprising one of the mixtures of peptides derived from the E6 protein HPV16 and one of the mixtures derived from the E7 protein of HPV16, as defined above.

Specifically:

the peptide E6 (14-34) binds with good affinity to the DRB1*0301, 0701 and 1501 molecules,
the peptide E6 (30-50) binds with good affinity to the DRB1*0101, 0301, 0401, 1101, 1301 and 1501, DRB5*0101 and DRB4*0101 molecules,
the peptide E6 (61-80) binds with good affinity to the DRB1*0301, 1101 and 1501, DRB3*0101 and DRB5*0101 molecules,
the peptide E6 (76-95) binds with good affinity to the DRB1*0101, 1101, 1301 and 1501, DRB5*0101 and DRB4*0101 molecules,
the peptide E6 (91-119) binds with good affinity to the DRB1*0101, 0301, 0401, 0701 and 1501 and DRB5*0101 molecules,
the peptide E7 (1-20) binds with good affinity to the DRB1*0101, 0301, 0401, 1101, 1301 and 1501, DRB5*0101 and DRB4*0101 molecules,
the peptide E7 (7-27) binds with good affinity to the DRB1*0101, 0301, 0401, 1101 and 1301, DRB3*0101, DRB5*0101 and DRB4*0101 molecules,
the peptide E7 (60-74) binds with good affinity to the DRB1*0701 and DRB5*0101 molecules,
the peptide E7 (65-87) binds with good affinity to the DRB1*0101, 0301, 0401, 0701 and 1501 and DRB3*0101 molecules,
the peptide E7 (78-98) binds with good affinity to the DRB1*0101, 0701, 1101 and 1501, DRB5*0101 and DRB4*0101 molecules.

The sequences of these various peptides are given in tables III and IV below:

TABLE III

| Peptide | Sequence | Identification number |
|---|---|---|
| E6(1-22) | MHQKRTAMFQDPQERPRKLPQL | SEQ ID No. 59 |
| E6(14-34) | ERPRKLPQLCTELQTTIHDII | SEQ ID No. 8 |
| E6(30-50) | IHDIILECVYCKQQLLRREVY | SEQ ID No. 10 |
| E6(45-67) | LRREVYDFAFRDLCIVYRDGNPY | SEQ ID No. 26 |
| E6(61-80) | YRDGNPYAVCDKCLKFYSKI | SEQ ID No. 11 |
| E6(76-95) | FYSKISEYRHYCYSLYGTTL | SEQ ID No. 12 |
| E6(91-110) | YGTTLEQQYNKPLCDLLIRC | SEQ ID No. 35 |
| E6(105-126) | DLLIRCINCQKPLCPEEKQRHL | SEQ ID No. 60 |
| E6(121-140) | EKQRHLDKKQRFHNIRGRWT | SEQ ID No. 41 |
| E6(135-158) | IRGRWTGRCMSCCRSSRTRRETQL | SEQ ID No. 44 |
| E7(1-20) | MHGDTPTLHEYMLDLQPETT | SEQ ID No. 14 |
| E7(7-27) | TLHEYMLDLQPETTDLYCYEQ | SEQ ID No. 15 |
| E7(21-40) | DLYCYEQLNDSSEEEDEIDG | SEQ ID No. 61 |
| E7(35-55) | EDEIDGPAGQAEPDRAHYNIV | SEQ ID No. 62 |
| E7(43-57) | GQAEPDRAHYNIVTF | SEQ ID No. 63 |
| E7(60-74) | KCDSTLRLCVQSTHV | SEQ ID No. 16 |
| E7(65-87) | LRLCVQSTHVDIRTLEDLLMGTL | SEQ ID No. 17 |
| E7(78-98) | TLEDLLMGTLGIVCPICSQKP | SEQ ID No. 18 |

TABLE IV

| Peptide | Sequence |
|---|---|
| E6/2 (14-34) | E R P R K L P Q L C T E L Q T T I H D I I |
| E6/17-31 | R K L P Q L C T E L Q T T I H |
| E6/20-34 | P Q L C T E L Q T T I H D I I |
| E6/24-38 | T E L Q T T I H D I I L E C V |
| E6/28-42 | T T I H D I I L E C V Y C K Q |

TABLE IV-continued

| Peptide | | Sequence |
|---|---|---|
| E6/3 (30-50) | | I H D I I L E C V Y C K Q Q L L R R E V Y |
| | E6/31-45 | H D I I L E C V Y C K Q Q L L |
| | E6/36-50 | E C V Y C K Q Q L L R R E V Y |
| E6/4 (45-67) | | L R R E V Y D F A F R D L C I V Y R D G N P Y |
| | E6/42-56 | Q Q L L R R E V Y D F A F R D |
| | E6/50-64 | Y D F A F R D L C I V Y R D G |
| | E6/55-69 | R D L C I V Y R D G N P Y A V |
| E6/6 (76-95) | | F Y S K I S E Y R H Y C Y S L Y G T T L |
| | E6/76-90 | F Y S K I S E Y R H Y C Y S L |
| | E6/78-92 | S K I S E Y R H Y C Y S L Y G |
| | E6/81-95 | S E Y R H Y C Y S L Y G T T L |
| | E6/84-98 | R H Y C Y S L Y G T T L E Q Q |
| E6/7 (91-110) | | Y G T T L E Q Q Y N K P L C D L L I R C |
| | E6/89-103 | S L Y G T T L E Q Q Y N K P L |
| | E6/93-107 | T T L E Q Q Y N K P L C D L L |
| | E6/97-111 | Q Q Y N K P L C D L L I R C I |
| | E6/101-115 | K P L C D L L I R C I N C Q K |
| E6/9 (121-140) | | E K Q R H L D K K Q R F H N I R G R W T |
| | E6/124-138 | H L D K K Q R F H N I R G R |
| | E6/130-144 | Q R F H N I R G R W T G R C M |
| E7/1 (1-20) | | M H G D T P T L H E Y M L D L Q P E T T |
| | E7/6-20 | P T L H E Y M L D L Q P E T T |
| E7/2 (7-27) | | T L H E Y M L D L Q P E T T D L Y C Y E Q |
| | E7/9-23 | H E Y M L D L Q P E T T D L Y |
| | E7/13-27 | L D L Q P E T T D L Y C Y E Q |
| E7/7 (65-87) | | L R L C V Q S T H V D I R T L E D L L M G T L |
| | E7/65-79 | L R L C V Q S T H V D I R T L |
| | E7/67-81 | L C V Q S T H V D I R T L E D |
| | E7/72-86 | T H V D I R T L E D L L M G T |
| E7/8 (78-98) | | T L E D L L M G T L G I V C P I C S Q K P |
| | E7/77-91 | R T L E D L L M G T L G I V C |
| | E7/84-98 | M G T L G I V C P I C S Q K P |

Other peptides exhibit binding activities, but on a limited number of molecules.

A subject of the present invention is also an immunogenic anti-HPV composition, characterized in that it comprises a mixture of peptides derived from an E6 protein of HPV and/or a mixture of peptides derived from an E7 protein of HPV, as defined above, combined with at least one pharmaceutically acceptable vehicle and, optionally, with at least one adjuvant.

The adjuvants used are adjuvants conventionally used in vaccine compositions, such as alumina hydroxide and squalene.

According to advantageous embodiment of said immunogenic composition, said peptides are either in the form of lipopeptides, or incorporated into a recombinant virus, a viral vector for gene therapy (adenovirus, etc.), or included in a protein and in particular a recombinant protein (Leclerc C. et al., Int. Rev. Immunol., 1994, 11, 2, 123-132; Janssen R. et al., Int. Rev. Immunol., 1994, 11, 2, 113-121), or chemically modified. In the latter case, they comprise, for example, unnatural modifications such as D amino acids, pseudopeptide bonds or modifications of the C- or N-terminal ends.

The lipid moiety of the lipopeptide is in particular obtained by addition of a lipid unit to an α-amino function of said peptides or to a reactive function of the side chain of an amino acid of the peptide moiety; it may comprise one or more optionally branched or unsaturated $C_4$-$C_{20}$ fatty acid-derived chains (palmitic acid, oleic acid, linoleic acid, linolenic acid, 2-aminohexadecanoic acid, pimelautide, trimetauxide) or a derivative of a steroid. The method for preparing such lipopeptides is in particular described in international applications WO 99/40113 and WO 99/51630. The preferred lipid moiety is in particular represented by an $N^{\alpha}$-acetyl-lysine $N^{\epsilon}$(palmitoyl) group, also referred to as Ac-K(Pam).

According to another advantageous embodiment of said immunogenic composition, said mixture of peptides is combined:

with one or more peptides or lipopeptides containing one or more CD8+ epitopes (specifically recognized by cytotoxic T lymphocytes and presented by HLA I molecules), and more particularly the CD8+ epitopes derived from an HPV protein, in particular from an HPV16 protein (Ressing et al., van Driel et al.) and/or with other peptides comprising multiple CD4+ epitopes, such as the tetanus toxin TT peptide (positions 830-846), the Influenza hemagglutinin HA peptide (positions 307-319), PADRE (Pan DR Epitope, Alexandre J. et al., Immunity, 1994, 1, 9, 751-761) or the *Plasmodium falciparum* LSA3 peptide and/or with one or more peptides or lipopeptides containing one or more B epitopes, more particularly B epitopes derived from an HPV16 protein (Tindle et al.), specifically recognized by antibodies directed against these epitopes.

The E6 and E7 peptides according to the invention, included in the mixtures, as defined above were advantageously selected using an HLA-DR/peptide binding assay comprising:

purifying the HLA-DR molecules of interest, i.e. those involving more than 5% of a given population, and in particular the HLA DR1, DR3, DR4, DR7, DR11, DR13 and DR15 molecules, incubating the HLA-DR molecules thus purified with various concentrations of overlapping fragments entirely covering the sequence of the E6 protein or of the E7 protein and with a reagent R1 or tracer consisting of a peptide fragment associated with a nonradioactive label, such as biotin, and the sequence of which is different from said peptides; the reagent R1 or tracer is chosen in such a way that it exhibits an affinity with respect to one of the HLA-DR molecules of interest, such that it may be used at a concentration <200 nM, transferring the complexes obtained onto an ELISA-type plate precoated with an antibody specific for all the HLA-DRs, revealing the HLA-DR molecule/reagent R1 complexes attached to the bottom of the plate by means of suitable conjugates, such as streptavidin-phosphatase, and of a fluorescent substrate, selecting the peptides comprising different epitopes, i.e. the most representative of the various regions of interaction between the E6 protein or the E7 protein and the HLA-DR molecules, and choosing the most suitable peptides, as a function of the frequency of the alleles with respect to which they exhibit a binding activity <1 000 nM, preferably <800 nM, corresponding to the concentration of these peptides which inhibits 50% of the binding of the reagent R1 ($IC_{50}$).

These assays make it possible to unambiguously associate with each allele of the 1st gene or of the 2nd gene the sequences of the fragments capable of binding thereto or, on the contrary, which do not bind thereto.

This approach makes it possible to define immunogenic compositions including peptides which bind to the greatest number of different HLA-DR molecules and which may thus be advantageously protective for the majority of patients, even if their HLA molecules are not known.

This approach also has the advantage of making it possible to select peptides which are significantly more specific with respect to HPV16 than the approaches seeking to select peptides on the basis of their ability to stimulate CD4+ T lymphocytes (proliferation assays).

The incubation conditions are specific to each HLA-DR molecule (incubation time, pH, reagent R1, concentration of HLA-DR or of peptide).

The reagent R1 is selected from the group consisting of the following sequences:

PKYVKQNTLKLAT (HA 306-318) (SEQ ID No. 1), specific for the alleles DRB1*0101, DRB1*0401, DRB1*1101, EAEQLRAYLDGTGVE (A3 152-166) (SEQ ID No. 2), specific for the allele DRB1*1501, AKTIAYDEEARGLE (MT 2-16) (SEQ ID No. 3), specific for the allele DRB1*0301, AAYAAAKAAALAA (YKL) (SEQ ID No. 4), specific for the allele DRB1*0701, TERVRLVTRHIYNREE (B1 21-36) (SEQ ID No. 5), specific for the allele DRB1*1301, ESWGAVWRIDTPDKLTGPFT (LOL 191-210) (SEQ ID No. 6), specific for the allele DRB3*0101, and AGDLLAIETDKATI (E2/E168) (SEQ ID No. 7), specific for the allele DRB4*0101.

Other reagents R1 can be used, in particular those described in Southwood et al. (24).

As a variant, said immunogenic composition advantageously comprises the sequences encoding the peptides as defined above.

In fact, the use of naked DNA for immunization constitutes an effective vaccinal approach: it consists in injecting into the host organism to be vaccinated a naked DNA encoding a protein antigen; this DNA allows sustained synthesis of the antigen by the host's cells and also long-lasting presentation of this antigen to the immune system.

A subject of the present invention is also a vaccine, characterized in that it includes an immunogenic composition as defined above.

A subject of the present invention is also peptides derived from an E6 protein of HPV, in particular of HPV16, and/or from an E7 protein of HPV, in particular of HPV16, characterized:

in that they contain a CD4+ epitope capable of having a binding activity <1 000 nM, preferably <800 nM with respect to at least one HLA II (HLA-DR) molecule predominant in Caucasian populations (1st gene and/or 2nd gene), as defined above, of being recognized by CD4+ T lymphocytes specific for said peptides, and of stimulating CD4+ T lymphocytes specific for said peptides, and in that they are selected from the group consisting of the fragments of sequence SEQ ID Nos. 8 to 18, 21-25, 28-34, 36-39, 42-43 and 45-52, corresponding respectively to the following peptides of the E6 protein of HPV16: the peptide E6 (14-34 or 14-45), the peptide E6 (30-50), the peptide E6 (61-80), the peptide E6 (76-95), the peptide E6 (91-119) and the peptides E6 (20-34, 24-38, 28-42, 31-45, 36-50, 42-56, 50-64, 55-69, 76-90, 78-92, 81-95, 84-98, 89-103, 93-107, 97-111, 101-115, 124-138, 130-144), or to the following peptides of the E7 protein of HPV16: the peptide E7 (1-20), the peptide E7 (7-27), the peptide E7 (60-74), the peptide E7 (65-87), the peptide E7 (78-98) and the peptides E7 (6-20, 9-23, 13-27, 65-79, 67-81, 72-86, 77-91, 84-98).

A subject of the present invention is a diagnostic reagent, characterized in that it is selected from one of the E6 and E7 peptides as defined above, said peptides optionally being labeled or complexed, in the form of multimeric complexes.

A subject of the present invention is also a method for evaluating the immune state of an individual, characterized in that it comprises a step of detecting the presence of CD4+ T cells specific for the E6 and/or E7 peptides as defined above; said detection is advantageously carried out using one of the following assays: proliferation assay, ELISPOT assay [see, for example, international application WO 99/51630 or Gahéry-Ségard et al. (27)] or flow cytometry in the presence of multimeric complexes made up of said E6 and/or E7 peptides.

More precisely:

as regards the proliferation assay:

A suspension of cells (PBMCs, CD8+ cell-depleted PBMCs, T lymphocytes pre-enriched by a step of culturing in vitro with the peptides selected according to the invention, or cloned T lymphocytes) is cultured for 3 to 5 days in the presence of the selected peptides and, as needed, of suitable presenting cells, such as dendritic cells, autologous or heterologous PBMCs, lymphoblastoid cells such as those obtained after infection with the EBV virus or genetically modified cells. The cell proliferation is measured by incorporation of tritiated thymidine into the DNA of the cells. The peptides selected in accordance with the invention make it possible to reveal, in the initial suspension, the presence of cells specific for these peptides.

as regards the ELISPOT assay:

The ELISPOT assay makes it possible to reveal the presence of T cells specific for a peptide selected in accordance with the invention and secreting γ-IFN.

More precisely, the T cells are revealed by measuring the secretion of γ-IFN after incubation of PBMCs from patients with the peptides selected according to the invention, in accordance with the method described in Gahéry-Ségard et al., 2000 (27).

as regards the use of multimeric complexes, and in particular of tetrameric complexes:

a biological sample, preferably peripheral blood mononuclear cells (PBMCs), is brought into contact with tetrameric complexes produced from multimeric complexes made up of E6 or E7 peptides as defined above—soluble and biotinylated HLA class II molecule, and the labeled cells are analyzed by flow cytometry.

Advantageously, prior to bringing the biological sample into contact with said complex, it is enriched in CD4+ T cells by bringing it into contact with anti-CD4 antibodies so as to enrich said sample.

The tetramers are prepared as specified, for example, in E. J. Novak et al. (J. Clin. Investig., 1999, 104, R63-R67) or in M. J. Kuroda et al. (J. Virol., 2000, 74, 18, 8751-8756).

Briefly the tetramers are produced by incubating, for 72 hours at 37° C. and in a 10 mM citrate phosphate buffer containing 0.15 M NaCl, at a pH of between 4.5 and 7, soluble and biotinylated HLA II molecules with a 10-fold excess of E6 or E7 peptides identified and selected in accordance with the invention.

The tetramerized form is obtained by adding streptavidin labeled with a fluorochrome to the preparation in an amount four times less (mole for mole) than HLA II molecules. The whole mixture is incubated overnight at ambient temperature.

To use these tetramers, a suspension of cells (PBMCs, CD8+ cell-depleted PBMCs, T lymphocytes pre-enriched by a step of culturing in vitro with the E6 or E7 peptides selected in accordance with the present invention, or cloned T lymphocytes) is brought into contact with one or more tetramers (10 to 20 mg/ml) for 1 to 3 hours. After washing, the suspension is analyzed by flow cytometry: the labeling of the cells with the tetramers is visualized by virtue of the fact that these constructs are fluorescent.

The flow cytometry makes it possible to separate the tetramer-lableled cells from the nonlabeled cells and thus to perform cell sorting.

A subject of the present invention is thus also a method for sorting HPV16-specific T lymphocytes, characterized in that it comprises at least the following steps:

incubating a suspension of cells to be sorted, or bringing it into contact, for 1 to 3 hours, with one or more tetramers formed from E6 and/or E7 peptide as defined above/soluble and biotinylated HLA II molecule complexes, and conjugated to streptavidin labeled with a fluorochrome, analyzing by flow cytometry, and sorting the tetramer-labeled cells.

Besides the arrangements above, the invention also comprises other arrangements which will emerge from the following description, which refers to examples of implementation of the method which is the subject of the present invention and also to the attached drawing, in which:

FIG. 1 represents the proliferation and the γ-IFN secretion of cells from a patient suffering from bowenoid papulosis and in whom the infection has been spontaneously resolved. The patient is DRB1*1601/1501 DRB5*0101. The peptide E6 (45-67) is a good ligand for DRB1*1501, and the peptide E7 (7-27) is a good ligand for DRB5*0101 (see also table VIII).

It should be clearly understood, however, that these examples are given purely by way of illustration of the subject of the invention, of which they in no way constitute a limitation.

EXAMPLE 1

Various HPV Strains and their Percentage Identity with HPV16

| Strains | Pathology | E6 | E7 |
|---------|-----------|-----|-----|
| HPV18 | Cervical cancer | 63 | 40 |
| HPV31 | idem | 72 | 81 |
| HPV33 | idem | 71 | 70 |
| HPV45 | idem | 63 | 44 |
| HPV58 | idem | 71 | 69 |
| HPV30 | idem | 59 | 50 |
| HPV34 | idem | 67 | 56 |
| HPV35 | idem | 79 | 83 |
| HPV39 | idem | 61 | 41 |
| HPV40 | idem | 44 | 40 |
| HPV42 | idem | 50 | 53 |
| PHV43 | idem | 48 | |
| HPV44 | idem | 47 | 52 |
| HPV51 | idem | 67 | 45 |
| HPV52 | idem | 69 | 68 |
| HPV56 | idem | 63 | 44 |
| HPV57 | idem | 48 | 44 |
| HPV10 | warts | 47 | 84 |

-continued

| Strains | Pathology | E6 | E7 |
|---------|-----------|----|----|
| HPV3 | idem | 46 | 56 |
| HPV4 | idem | 38 | 69 |

EXAMPLE 2

Principle of the Binding Assays

Peptide Synthesis

The peptides chosen cover the sequence of the E6 protein or of the E7 protein. All the peptides were synthesized according to the Fmoc strategy by parallel solid-phase synthesis, purified by HPLC and controlled by mass spectrometry (ES-MS).

Purification of HLA-DR Molecules

The HLA-DR molecules were purified from various homozygous EBV lines by immunoaffinity. The method described in Southwood et al. (24) can in particular be used. Their origin and the various alleles which characterize them are described in table IV.

TABLE IV

| Lines | Specificities | DRB1 alleles | Other DRB alleles |
|-------|---------------|--------------|-------------------|
| LG2 (14) | HLA-DR1 | DRB1*0101 | — |
| HOM2 | | | |
| SCHU | HLA-DR2 | DRB1*1501 | DRB5*0101 |
| MAT (14) | HLA-DR3 | DRB1*0301 | DRB3*0101 |
| STEILIN | | | |
| BOLETH | HLA-DR4 | DRB1*0401 | DRB4*0101 |
| PREISS (14) | | | |
| PITOUT (14) | HLA-DR7 | DRB1*0701 | DRB4*0101 |
| SWEIG (14) | HLA-DR11 | DRB1*1101 | DRB3*0202 |
| HHKB (17) | HLA-DR13 | DRB1*1301 | DRB3*0101 |

The monomorphic antibody specific for the HLA-DR molecules is in particular that described in Southwood et al. (24) or that described in Posch et al. (25). The antibodies are purified from culture supernatants on protein A-sepharose columns. These antibodies are coupled to sepharose 4B or protein A-sepharose columns for purification of the HLA-DR molecules.

HLA-DR/Peptide Binding Assays

The assays for binding of the peptides to the HLA-DR molecules are competition assays with immuno-enzymatic revelation, initially developed by Hill on the HLA-DR molecule (26). They are carried out in 96-well plates, which makes it possible to study many samples in the same experiment. Briefly, the purified HLA-DR molecules are incubated with a biotinylated peptide which serves as a tracer and various concentrations of test peptide.

After incubation for 24 to 72 hours, these samples are neutralized, and then 100 µl of each sample are transferred onto an ELISA plate precoated with the HLA-DR molecule-specific monomorphic antibody. The HLA-DR molecule/biotinylated peptide complexes, attached to the bottom of the plate via the HLA-DR molecule-specific monomorphic antibody, are revealed by means of streptavidin-phosphatase conjugate and a fluorescent substrate. The activity of each peptide is characterized by the concentration of this peptide which inhibits 50% of the binding of the biotinylated peptide ($IC_{50}$).

Choice and Optimization of the Binding Assays

Choice of Alleles (1st Gene)

The alleles studied are all the alleles of the French population whose frequency exceeds 5% of the population.

They are the alleles DRB1*0101, DRB1*0301, DRB1*0401, DRB1*0701, DRB1*1101, DRB1*1301 and DRB1*1501 (table I). They represent, by themselves, 53 to 82% of the alleles of Caucasian populations and make up various specificities of the HLA-DR series.

Choice of Alleles (2nd Gene)

The alleles studied are the alleles most commonly encountered. They are the alleles HLA-DRB3*0101, HLA-DRB4*0101 and HLA-DRB5*0101.

Assay Specificity

The choice of the biotinylated peptides is the determining element of the assay specificity. Most of the cells used possess two different HLA-DR molecules (encoded by two alleles) which are both purified by an HLA-DR molecule-specific monomorphic antibody and are both recognized by the same antibody. In order to unambiguously study the binding of a peptide to the DRB1 allele, it is necessary to be sure that the biotinylated peptide binds this allele and does not bind the product of the other allele.

For this purpose, the peptides as defined as reagents R1 above were used.

Assay Conditions and Sensitivity

For each HLA-DRB1 molecule, the concentration of MHC II molecules, the concentration of the biotinylated peptide, the incubation pH and the incubation time were optimized as specified in table V below.

TABLE V

| Alleles | Protein concentration (µg/ml) | Tracers | Tracer concentration (nM) | Optimum pH | Incubation time (h) |
|---------|------|---------|------|-----|----|
| DRB1*0101 | 0.6 | HA 306-318 | 10 | 6 | 24 |
| DRB1*0301 | 2.3 | MT 2-16 | 50 | 4.5 | 72 |
| DRB1*0401 | 1.6 | HA 306-318 | 30 | 6 | 24 |
| DRB1*0701 | 0.4 | YKL | 10 | 5 | 24 |
| DRB1*1101 | 1.3 | HA 306-318 | 20 | 5 | 24 |
| DRB1*1301 | 0.7 | B1 21-36 | 200 | 4.5 | 72 |
| DRB1*1501 | 0.5 | A3 152-166 | 10 | 4.5 | 24 |

The sensitivity of each assay is reflected by the $IC_{50}$ values observed with the nonbiotinylated peptides which correspond to the tracers, and the results obtained are given in table VI below.

TABLE VI

| Alleles | Frequency | Biotinylated peptides | Sequences | $IC_{50}$ (Nm) |
|---------|-----------|----------------------|-----------|----------------|
| DRB1*0101 | 9.3 | HA 306-318 | PKYVKQNTLKLAT | 31 |
| DRB1*0401 | 5.6 | HA 306-318 | PKYVKQNTLKLAT | 44 |
| DRB1*1101 | 9.2 | HA 306-318 | PKYVKQNTLKLAT | 38 |
| DRB1*0701 | 14.0 | YKL | AAYAAAKAAALAA | 34 |

TABLE VI-continued

| Alleles | Frequency | Biotinylated peptides | Sequences | $IC_{50}$ (Nm) |
|---|---|---|---|---|
| DRB1*0301 | 10.9 | MT 2-16 | AKTIAYDEEARRGLE | 100 |
| DRB1*1301 | 6.0 | B1 21-36 | TERVRLVTRHIYNREE | 330 |
| DRB1*1501 | 8.0 | A3 152-166 | EAEQLRRAYLDGTGVE | 14 |
| DRB5*0101 | 7.9 | HA 306-318 | PKYVKQNTLKLAT | 6.5 |
| DRB3*0101 | 9.2 | Lol 191-210 | ESWGAVWRIDTPDKLTGPFT | 5 |
| DRB4*0101 | 28.4 | E2/E168 | AGDLLAIETDKATI | 2 |

The frequencies indicated are the allelic frequencies in France and are representative of those of the Caucasian population. They are derived from Colombani (22).

Tables VIIa and VIIb below illustrate the binding activity of the peptides according to the invention, measured under the conditions specified above.

TABLE VIIa

Binding activities of the selected E6 and E7 peptides with respect to the HLA-DR molecules which are predominant in the Caucasian population

| | DR1 | DR3 | DR4 | DR7 | DR11 | DR13 | DR15 | B3 | B5 | B4 |
|---|---|---|---|---|---|---|---|---|---|---|
| E6/1 (1-22) | >10000 | 3500 | >10000 | >10000 | >10000 | >10000 | >10000 | 10000 | >10000 | >10000 |
| E6/2 (14-34) | 3500 | 550 | >10000 | 225 | 10000 | >10000 | 800 | 1450 | >10000 | >10000 |
| E6/3 (30-50) | 400 | 1000 | 450 | 1400 | 800 | 250 | 75 | 1500 | 3.5 | 700 |
| E6/4 (45-67) | 50 | >10000 | 2000 | 2330 | 125 | >10000 | 225 | 2500 | 65 | >10000 |
| E6/5 (61-80) | 1750 | 100 | 2500 | 10000 | 60 | >10000 | 400 | 200 | 9.5 | 6500 |
| E6/6 (76-95) | 3.5 | >10000 | 5000 | 3500 | 150 | 300 | 24 | >10000 | 120 | 27 |
| E6/7 (91-110) | 30 | 200 | 90 | 500 | 2000 | >10000 | 5.5 | 9500 | 50 | 6500 |
| E6/8 (105-126) | 1750 | >10000 | 3750 | >10000 | 5000 | 5000 | 4000 | >10000 | 30 | 70 |
| E6/9 (121-140) | 125 | >10000 | >10000 | 200 | 350 | 1130 | >10000 | >10000 | 85 | >10000 |
| E6/10 (135-158) | 200 | >10000 | 17.5 | 10000 | 700 | >10000 | 1600 | >10000 | 10 | 4250 |
| E7/I (1-20) | 2500 | >10000 | 300 | >10000 | 1750 | >10000 | 125 | 35 | >10000 | 4 |
| E7/II (7-27) | 300 | 560 | 60 | >10000 | 600 | 7500 | 1770 | 8.5 | 70 | 375 |
| E7/III (21-40) | >10000 | 4600 | 1750 | >10000 | >10000 | >10000 | 5300 | >10000 | >10000 | >10000 |
| E7/IV (35-55) | >10000 | >10000 | >10000 | >10000 | >10000 | >10000 | >10000 | >10000 | >10000 | >10000 |
| E7/V (43-57) | >10000 | >10000 | >10000 | >10000 | >10000 | >10000 | 2000 | >10000 | 2250 | >10000 |
| E7/VI (60-74) | 5000 | >10000 | 2000 | 900 | 7000 | >10000 | >10000 | >10000 | 200 | 1950 |
| E7/VII (65-87) | 650 | 450 | 650 | 900 | 2000 | >10000 | 470 | 850 | 2000 | 2000 |
| E7/VIII (78-98) | 800 | >10000 | 2250 | 500 | 900 | >10000 | 35 | >10000 | 350 | 500 |

TABLE VIIb

Binding activities of the selected E6 and E7 peptides with respect to the HLA-DR molecules which are predominant in a Caucasian population

| peptide | SEQ ID No. e | DR1 | DR3 | DR4 | DR7 | DR11 | DR13 | DR15 | DRB3 | DRB4 | DRB5 |
|---|---|---|---|---|---|---|---|---|---|---|---|
| E6/2 (14-34) | No. 8 | | | | | | | | | | |
| E6 17-31 | No. 20 | | 10000 | | 6500 | | | 1750 | | | |
| E6 20-34 | No. 21 | 45 | >10000 | >10000 | 7000 | | | >10000 | | | |
| E6 24-38 | No. 22 | 425 | 300 | >10000 | 1500 | 300 | >10000 | 950 | | >10000 | >10000 |
| E6 28-42 | No. 23 | 45 | >10000 | 1200 | >10000 | 2000 | >10000 | 450 | | 4250 | 50 |

TABLE VIIb-continued

Binding activities of the selected E6 and E7 peptides
with respect to the HLA-DR molecules which are
predominant in a Caucasian population

| peptide | SEQ ID No. e | DR1 | DR3 | DR4 | DR7 | DR11 | DR13 | DR15 | DRB3 | DRB4 | DRB5 |
|---|---|---|---|---|---|---|---|---|---|---|---|
| E6/3 (30-50) | No. 10 | | | | | | | | | | |
| E6 31-45 | No. 24 | 65 | >10000 | 2250 | | 600 | 10000 | 750 | | >10000 | 95 |
| E6 36-50 | No. 25 | 38 | 2750 | 5000 | | 525 | >10000 | 225 | | >10000 | 15 |
| E6/4 (45-67) | No. 26 | | | | | | | | | | |
| E6 42-56 | No. 28 | >10000 | >10000 | >10000 | | 6000 | 375 | 3250 | | 55 | >10000 |
| E6 50-64 | No. 29 | 900 | | | | 85 | 6500 | 1483 | | | 60 |
| E6 55-69 | No. 30 | 1500 | | | | 250 | | 55 | | | >10000 |
| E6/6 (76-95) | No. 12 | | | | | | | | | | |
| E6 76-90 | No. 31 | 125 | | | | 525 | 225 | 500 | | >10000 | 1050 |
| E6 78-92 | No. 32 | 225 | | | | 1750 | 2250 | 120 | | >10000 | 1250 |
| E6 81-95 | No. 33 | 10 | | | | 725 | >10000 | >10000 | | >10000 | 2500 |
| E6 84-98 | No. 34 | | | 2000 | 3250 | 7000 | >10000 | >10000 | | >10000 | 900 |
| E6/7 (91-110) | No. 35 | | | | | | | | | | |
| E6 89-103 | No. 36 | 125 | | 5000 | 1500 | >10000 | >10000 | 53 | | >10000 | 200 |
| E6 93-107 | No. 37 | 5 | | >10000 | 7750 | | | 18 | | | 325 |
| E6 97-111 | No. 38 | 575 | 1233 | 325 | >10000 | | | 4000 | | | 5500 |
| E6 101-115 | No. 39 | 12 | 3000 | 25 | 350 | | | 150 | | | 5 |
| E6/9 (121-140) | No. 41 | | | | | | | | | | |
| E6 124-138 | No. 42 | 10 | | | >10000 | 475 | | | | | 75 |
| E6 130-144 | No. 43 | 4 | | | 950 | 115 | | | | | 75 |
| E7/1 (1-20) | No. 14 | | | | | | | | | | |
| E7 6-20 | No. 45 | 750 | >10000 | 175 | | 1500 | | 675 | 90 | 200 | 2000 |
| E7/2 (7-27) | No. 15 | | | | | | | | | | |
| E7 9-23 | No. 46 | 325 | >10000 | 375 | | 9500 | | | 65 | >10000 | >10000 |
| E7 13-27 | No. 47 | 4000 | 3500 | 4250 | | 3500 | | | 10000 | >10000 | >10000 |
| E7/7 (65-87) | No. 17 | | | | | | | | | | |
| E7 65-79 | No. 48 | 750 | >10000 | >10000 | 600 | | | >10000 | >10000 | | |
| E7 67-81 | No. 49 | 7000 | >10000 | 7500 | 1500 | | | 950 | >10000 | | |
| E7 72-86 | No. 50 | 25 | 900 | 100 | 2000 | | | 35 | 600 | | |
| E7/8 (78-98) | No. 18 | | | | | | | | | | |
| E7 77-91 | No. 51 | 5 | | | 55 | | | >10000 | | >10000 | 700 |
| E7 84-98 | No. 52 | 20 | | | 1250 | | | 425 | | 1750 | 90 |

The results are expressed in the form of concentrations giving 50% inhibition of maximum binding. The unit is nM.

EXAMPLE 3

Proliferation Assay

To verify the stimulation of CD4+ T cell proliferation using immunogenic composition according to the invention, a proliferation assay is performed in vitro.

The cells (PBMCs) extracted from peripheral blood were cultured in 96-well microplates in a proportion of $2 \times 10^5$ cells per well, in a final volume of 200 µl of complete medium. The cells were or were not stimulated with 10 µg/ml of a mixture of peptides according to the invention. After culturing for 5 days at 37° C., the cells were incubated overnight with 0.25 µCi of [$^3$H]-thymidine (Amersham, Life technology). The cells were recovered and the [$^3$H]-thymidine incorporation was measured in a cellular DNA.

Stimulation of the CD4+ T cells is effectively observed.

Other cells can be used: CD8+ cell-depleted PBMCs, T cells pre-enriched by a step of culturing in vitro with the peptides as defined above, or cloned lymphocytes.

Briefly, the enriching protocol is as follows:

The PBMCs, separated on a Ficoll gradient, are cultured at 37° C. in the presence of 0.1 to 10 mg/ml of peptides in RPMI medium supplemented with 10% human serum. On the 7th and 11th day of culturing, 50 units of recombinant human IL-2 are added to the culture. The cells are harvested on the 14th day.

EXAMPLE 4

Elispot

The ELISPOT makes it possible to detect cells which are specific for a peptide and which secrete a given cytokine.

50 µl/well of murine anti-human γ-IFN antibody diluted, in PBS buffer, to a concentration of 4 µg/ml are incubated in nitrocellulose-bottomed 96-well plates overnight at 4° C. in a humid chamber.

The wells are washed with PBS and saturated with RPMI medium containing 10% calf serum for 2 hours at 37° C.

If needed, suitable presenting cells, such as autologous or heterologous PBMCs, lymphoblastoid cells obtained after infection with the EBV virus or genetically modified cells, are used and are dispensed into the wells. The E6 or E7 peptides as defined in the invention are then added at various concentrations (10, 5 and 1 µg/ml).

The effector cells (PBMCs, CD8+ cell-depleted PBMCs, T lymphocytes pre-enriched by a step of culturing in vitro with the E6 or E7 peptides or both, or cloned lymphocytes) are added to the 96-well plates in a proportion of 20 000 cells/well.

The culture is incubated for 24 hours at 37° C. in an atmosphere containing 5% $CO_2$.

The plates are then washed and incubated for 2 hours with 100 µl of a rabbit antiserum specific for human γ-IFN.

After washing, an anti-rabbit IgG antibody conjugated to biotin then streptavidin conjugated to alkaline phosphatase are added successively for 1 hour.

Finally, the spots are revealed by virtue of a chromogenic substrate of alkaline phosphatase. These spots are counted under a microscope. Negative controls are given by the wells containing no peptides. The positive controls are provided by the wells containing mitogenic agents such as ionomycin (500 ng/ml) and phytohemagglutinin (PHA) (10 μg/ml).

EXAMPLE 5

In vivo Assay

The mixtures of peptides as defined above were assayed in vivo, in patients having bowenoid papulosis. Bowenoid papulosis is a cutaneous-mucosal infection due to HPV16 which affects young women; it is a chronic and recurring disease, despite the destructive treatments used. This disease is a vulvar intraepithelial neoplasm grade 3 from the beginning (VIN 3), which has the particularity of not progressing to an invasive carcinoma.

The considerable infiltration of the epithelium by numerous CD4+ lymphocytes suggests that these cells contribute to controlling the stage of the disease and to preventing invasion.

The results observed in a patient who had resolved the infection herself are given by way of example in FIG. 1.

The proliferative response of the cells from 13 patients having bowenoid papulosis, with respect to the peptides, was studied.

The peptides recognized, in terms of proliferation, by the CD4+ T lymphocytes were listed for each disease.

The results obtained are given in table VIII below.

This table shows the advantage of the peptides selected in accordance with the present invention.

TABLE VIII

| Patients | 1st DR | 2nd DR | 1st DR | 2nd DR | Prolif | Possible DR | Reminder IC$_{50}$ | ELISPOT | Possible DR | Reminder IC$_{50}$ |
|---|---|---|---|---|---|---|---|---|---|---|
| GUI | 1601 | (?) DRB5 | 1501 | (?) DRB5 | E6/2 | 1501 | 800 | E6/4 | 1501 | 225 |
|  |  |  |  |  |  | DRB5 | >10 000 |  | DRB5 | 65 |
|  |  |  |  |  | E6/4 | 1501 | 225 | E7/2 | 1501 | 1 770 |
|  |  |  |  |  |  | DRB5 | 65 |  | DRB5 | 70 |
|  |  |  |  |  |  |  |  | E7/3 | 1501 | 5 300 |
|  |  |  |  |  |  |  |  |  | DRB5 | >10 000 |
| CAR | 701 | (?) DRB4 |  |  | E6/2 | 701 | 225 |  |  |  |
|  |  |  |  |  |  | DRB4 | >10 000 |  |  |  |
|  |  |  |  |  | E7/2 | 701 | >10 000 |  |  |  |
|  |  |  |  |  |  | DRB4 | 375 |  |  |  |
| JOU | 1501 | (?) DRB5 |  |  | E6/2 | 1501 | 800 |  |  |  |
|  |  |  |  |  |  | DRB5 | >10 000 |  |  |  |
|  |  |  |  |  | E6/4 | 1501 | 225 |  |  |  |
|  |  |  |  |  |  | DRB5 | 65 |  |  |  |
|  |  |  |  |  | E6/5 | 1501 | 400 |  |  |  |
|  |  |  |  |  |  | DRB5 | 9.5 |  |  |  |
|  |  |  |  |  | E6/10 | 1501 | 1 600 |  |  |  |
|  |  |  |  |  |  | DRB5 | 10 |  |  |  |
|  |  |  |  |  | E7/2 | 1501 | 1 770 |  |  |  |
|  |  |  |  |  |  | DRB5 | 70 |  |  |  |
| RIZ | 1501 | (?) DRB5 | 0404 or 0101 | 423 | weak | 1501 | 400 |  |  |  |
|  |  |  |  |  | E6/5 | DRB5 | 9.5 |  |  |  |
|  |  |  |  |  | weak | 1501 | 1 600 |  |  |  |
|  |  |  |  |  | E6/10 | DRB5 | 10 |  |  |  |
| ROU | 411 | (?) DRB4 | 701 | (?) DRB4 | weak |  |  |  |  |  |
| ALB | 1301 | (?) DRB3 | 1101 | (?) | uninterpretable |  |  |  |  |  |
| LOK | 1501 | (?) DRB5 | 801 |  | negative |  |  |  |  |  |
| ALC | 311 | (?) DRB3 | 1501 | (?) | E6/2 | 1501 | 800 | E6/2 | 1501 | 800 |
|  |  |  |  |  |  | DRB5 | >10 000 |  | DRB5 | >10 000 |
|  |  |  |  |  | E6/4 | 1501 | 225 | E6/4 | 1501 | 225 |
|  |  |  |  |  |  | DRB5 | 65 |  |  |  |
|  |  |  |  |  | E6/5 | 1501 | 400 |  |  |  |
|  |  |  |  |  |  | DRB5 | 9.5 |  |  |  |
|  |  |  |  |  | E6/7 | 1501 | 5.5 |  |  |  |
|  |  |  |  |  |  | DRB5 | 50 |  |  |  |
|  |  |  |  |  | E6/8 | 1501 | 4 000 |  |  |  |
|  |  |  |  |  |  | DRB5 | 30 |  |  |  |
|  |  |  |  |  | E7/2 | 1501 | 1 770 |  |  |  |
|  |  |  |  |  |  | DRB5 | 70 |  |  |  |
|  |  |  |  |  | E7/3 | 1501 | 5 300 |  |  |  |
|  |  |  |  |  |  | DRB5 | >10 000 |  |  |  |
|  |  |  |  |  | E7/4 | 1501 | >10 000 |  |  |  |
|  |  |  |  |  |  | DRB5 | >10 000 |  |  |  |
|  |  |  |  |  | E7/7 | 1501 | 470 |  |  |  |
|  |  |  |  |  |  | DRB5 | 2 000 |  |  |  |
|  |  |  |  |  | E7/8 | 1501 | 35 |  |  |  |
|  |  |  |  |  |  | DRB5 | 350 |  |  |  |
| BRO | 1101 | (?) DRB3 | 1001 |  | E6/2 | 1101 | 10 000 |  |  |  |
|  |  |  |  |  |  | DRB3 | 1 450 |  |  |  |
|  |  |  |  |  | E6/4 | 1101 | 125 |  |  |  |
|  |  |  |  |  |  | DRB3 | 2 500 |  |  |  |
| BLAI | 1101 | (?) DRB3 | 701 | (?) DRB4 | E6/2 | 1101 | 10 000 |  |  |  |
|  |  |  |  |  |  | (?) DRB3 | 1 450 |  |  |  |
|  |  |  |  |  |  | 701 | 225 |  |  |  |
|  |  |  |  |  |  | (?) DRB4 | >10 000 |  |  |  |

TABLE VIII-continued

| Patients | 1st DR | 2nd DR | 1st DR | 2nd DR | Prolif | Possible DR | Reminder IC$_{50}$ | ELISPOT | Possible DR | Reminder IC$_{50}$ |
|---|---|---|---|---|---|---|---|---|---|---|
| | | | | | E6/4 | 1101 | 125 | | | |
| | | | | | | (?) DRB3 | 2 500 | | | |
| | | | | | | 701 | 2 330 | | | |
| | | | | | | (?) DRB4 | >10 000 | | | |
| LEG | 1501 | (?) DRB5 | 801 | (?) | E6/2 | 1501 | 800 | | | |
| | | | | | | DRB5 | >10 000 | | | |
| | | | | | E6/7 | 1501 | 5.5 | | | |
| | | | | | | DRB5 | 60 | | | |
| | | | | | E7/7 | 1501 | 470 | | | |
| | | | | | | DRB5 | 2 000 | | | |
| | | | | | E6/10 | 1501 | 1 600 | | | |
| | | | | | | DRB5 | 10 | | | |
| CAI | 701 | (?) DRB4 | 1501 | (?) DRB5 | E6/2 | 1501 | 800 | | | |
| | | | | | | DRB5 | >10 000 | | | |
| | | | | | | 701 | 225 | | | |
| | | | | | | DRB4 | >10 000 | | | |
| | | | | | E6/4 | 1501 | 225 | | | |
| | | | | | | DRB5 | 65 | | | |
| | | | | | | 701 | 2 330 | | | |
| | | | | | | DRB4 | >10 000 | | | |
| DEL | 701 | (?) DRB4 | | | E6/2 | 701 | 225 | E6/2 | 701 | 225 |
| | | | | | | DRB4 | >10 000 | | DRB4 | >10 000 |
| | | | | | E6/4 | 701 | 2 330 | E6/4 | 701 | 2 330 |
| | | | | | | DRB4 | >10 000 | | DRB4 | >10 000 |

BIBLIOGRAPHICAL REFERENCES

1. Lowy D. R. et al., *Proc. Natl. Acad. Sci. USA*, 1994, 91, 2436.
2. Borysiewicz L. K. et al., *Lancet*, 1996, 347, 1523.
3. Ressing M. E. et al., *J. Immunother.*, 2000, 23, 255.
4. Van Driel W. J. et al., *Eur. J. Cancer*, 1999, 35, 946.
5. Ridge J. P., *Nature*, 1998, 393, 474.
6. Schoenberger S. P. et al., *Nature*, 1998, 393, 480.
7. Bennett S. R. et al., *Nature*, 1998, 393, 478.
8. Toes R. E. M. et al., *Semin. Immunol.*, 1998, 10, 443.
9. Tindle R. W. et al., *Proc. Natl. Acad. Sci. USA*, 1991, 88, 5887.
10. Azoury-Ziadeh R. K. et al., *Viral. Immunol.*, 1999, 12, 297.
11. Hohn H. et al., *J. Immunol.*, 1999, 163, 5715.
12. Hohn H. et al., *J. Virol.*, 2000, 74, 6632.
13. Bontkes H. J. et al., *J. Gen. Virol.*, 1999, 80, 409.
14. Strang G. et al., *J. Gen. Virol.*, 1990, 71, 423.
15. Altmann A. et al., *Eur. J. Cancer*, 1992, 28, 326.
16. Luxton J. C. et al., *J. Gen. Virol.*, 1996, 77, 1585.
17. Tsukui T. et al., *Cancer Res.*, 1996, 56, 3967.
18. Nakagawa M. et al., *Clin. Diagn. Lab. Immunol.*, 1996, 3, 205.
19. Kadish A. S. et al., *J. Natl. Cancer Inst.*, 1997, 89, 1285.
20. de Gruijl T. D. et al., *Cancer Res.*, 1998, 58, 1700.
21. Doan T. et al., *J. Virol.*, 1999, 74, 6166.
22. Colombani J., 1993, HLA: *fonctions immunitaires et applications médicales*, Eds. John Libbey Eurotext.
23. Ressing M. E. et al., *J. Immunol.*, 1995, 154, 5934.
24. Southwood et al., *J. Immunol.*, 1998, 160, 3363-3373.
25. Posch et al., *Eur. J. Immunol.*, 1996, 26, 1884.
26. Hill et al., *J. Immunol.*, 1994, 152, 2890.
27. Gahéry-Ségard et al., *J. Virol.*, 2000, 74, 1694.

The invention claimed is:

1. An isolated composition of a mixture of at least two peptides derived from an E6 protein of an HPV involved in cervical cancer or benign lesions of the skin, wherein:

each of the peptides included in the mixture binds, with a binding activity <1000 nM, to at least one HLA-DRB1 molecule the frequency of which is greater than 5% in the Caucasian population, the mixture of peptides binding to at least eight HLA class II molecules, the frequency of which is greater than 5% in the Caucasian population, encoded by the alleles selected from the group consisting of the alleles HLA DRB1*0101, HLA DRB1*0401, HLA DRB1*0701, HLA DRB1*1101, HLA DRB1*1301, HLA DRB1*1501, HLA DRB3*0101, HLA DRB4*0101 and HLA DRB5*0101, one of the peptides has at least 95% identity to SEQ ID NO: 21; and one of the peptides has at least 95% identity to SEQ ID NO: 26.

2. The composition of claim 1, wherein one of the peptides has at least 99% identity to SEQ ID NO: 21; and one of the peptides has at least 99% identity to SEQ ID NO: 26.

3. An immunogenic anti-HPV16 composition comprising a mixture of peptides derived from an E6 protein of HPV according to claim 1, combined with at least one pharmaceutically acceptable vehicle.

4. The composition according to claim 3, wherein the peptides are in the form of lipopeptides.

5. A vaccine comprising an immunogenic composition according to claim 3.

6. The composition of claim 1, wherein each of the peptides further binds to at least one HLA-DRB3, HLA-DRB4 or HLA-DRB5 molecule.

7. The composition of claim 3, wherein each of the peptides binds to at least one of said HLA II molecules with a binding activity <1,000 nM.

8. The composition of claim 7, wherein each of the peptides binds to at least one of said HLA II molecules with a binding activity <800 nM.

9. The composition of claim 1, wherein the mixture of peptides binds to at least eight HLA class II molecules, the frequency of which is greater than 5% in the Caucasian population.

10. The composition of claim 9, wherein the at least eight HLA class II molecules are encoded by the alleles selected from the group consisting of HLA DRB1*0101, DRB1*0401, DRB1*0701, DRB1*1101, DRB1*1301, and DRB1*1501 (DR1, DR3, DR4, DR7, DR11, DR13 and DR15 molecules) and HLA DRB3*0101, DRB4*0101 and DRB5*0101 (B3, B4 and B5).

* * * * *